(12) United States Patent
Shimizu et al.

(10) Patent No.: US 7,981,204 B2
(45) Date of Patent: Jul. 19, 2011

(54) PORPHYRAZINE COLORING MATTER AND INK COMPOSITION CONTAINING THE SAME

(75) Inventors: Shinsuke Shimizu, Tokyo (JP); Takashi Yoneda, Tokyo (JP)

(73) Assignee: Nippon Kayaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 12/810,376

(22) PCT Filed: Dec. 25, 2008

(86) PCT No.: PCT/JP2008/003947
§ 371 (c)(1),
(2), (4) Date: Jun. 24, 2010

(87) PCT Pub. No.: WO2009/084195
PCT Pub. Date: Jul. 9, 2009

(65) Prior Publication Data
US 2010/0279082 A1 Nov. 4, 2010

(30) Foreign Application Priority Data
Dec. 28, 2007 (JP) ................................. 2007-338523

(51) Int. Cl.
C09D 11/02 (2006.01)
C07D 487/22 (2006.01)
B32B 3/10 (2006.01)
B41J 2/01 (2006.01)

(52) U.S. Cl. ...................... 106/31.47; 540/124; 540/126; 428/195.1; 347/100

(58) Field of Classification Search ............... 106/31.47; 540/124, 126; 428/195.1; 347/100
See application file for complete search history.

(56) References Cited

U.S. PATENT DOCUMENTS

| | | | |
|---|---|---|---|
| 2,276,918 A | 3/1942 | Bienert et al. |
| 3,622,263 A | 11/1971 | Groll et al. |
| 4,952,688 A | 8/1990 | Springer |
| 5,123,960 A | 6/1992 | Shirota et al. |
| 5,279,622 A | 1/1994 | Stawitz et al. |
| 5,847,111 A | 12/1998 | Wald et al. |
| 5,922,116 A | 7/1999 | Mistry et al. |
| 6,149,722 A | 11/2000 | Robertson et al. |
| 6,190,422 B1 | 2/2001 | Carr |
| 6,238,827 B1 | 5/2001 | Nakazawa et al. |
| 6,379,441 B1 | 4/2002 | Kanaya et al. |
| 6,569,212 B2 | 5/2003 | Carr |
| 7,022,171 B2 | 4/2006 | Patel et al. |
| 7,034,149 B2 | 4/2006 | Hirokazu et al. |
| 7,097,701 B2 | 8/2006 | Tateishi et al. |
| 7,132,012 B2 | 11/2006 | Tateishi et al. |
| 7,160,372 B2 | 1/2007 | Yoshizawa et al. |
| 7,270,701 B2 | 9/2007 | Jinnou et al. |
| 7,282,090 B2 | 10/2007 | Osumi et al. |
| 7,314,273 B2 | 1/2008 | Robertson et al. |
| 7,419,537 B2 | 9/2008 | Fujii et al. |
| 7,566,362 B2 | 7/2009 | Mori et al. |
| 7,585,361 B2 | 9/2009 | Yoneda et al. |
| 7,591,888 B2 * | 9/2009 | Fujii et al. .................. 106/31.47 |
| 7,611,571 B2 | 11/2009 | Yamashita et al. |
| 7,854,797 B2 | 12/2010 | Fujii et al. |
| 2002/0128249 A1 | 9/2002 | Cook |
| 2004/0045478 A1 | 3/2004 | Tateishi et al. |

(Continued)

FOREIGN PATENT DOCUMENTS

DE 728 931 C 12/1942

(Continued)

OTHER PUBLICATIONS

International Search Report dated Mar. 17, 2009 in corresponding PCT/JP2008/003947.
International Search Report dated May 18, 2004 in PCT/JP2004/004446.
European Search Report dated May 30, 2007 in EP04724180.
International Search Report dated Jul. 10, 2007 in PCT/JP2007/057651.
XP-002435570; H.R. Schweizer; May 19, 1964;Farbstoffe;"Cyclo-tetraisoindolenin-(endo-isoindolenino)-Komplex," p. 510-511.

(Continued)

*Primary Examiner* — Helene Klemanski
(74) *Attorney, Agent, or Firm* — Nields, Lemack & Frame, LLC

(57) ABSTRACT

The present invention relates to a porphyrazine coloring matter represented by the following formula (1) or a salt thereof:

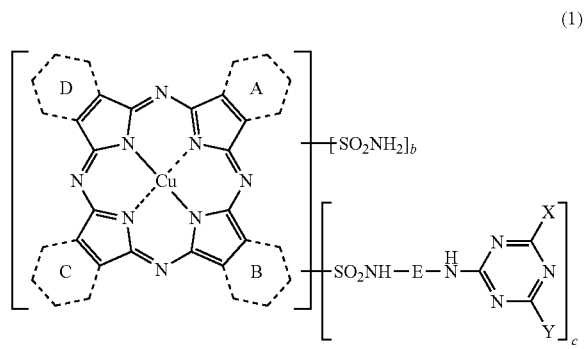

(1)

wherein, the rings A, B, C and D shown by broken lines each independently represent a 6-membered ring having aromaticity, at least 1.0 of said rings A to D is a benzene ring and at least 0.5 of them is a nitrogen-containing heteroaromatic ring, when shown as an average value; E represents an alkylene group; X and Y are each independently an anilino group having 1 to 3 carboxy groups; and b is 0 to 3.4, c is 0.1 to 3.5, and the sum of b and c is 1.0 to 3.5, when shown as an average value. The present invention can provide a porphyrazine coloring matter suitable for inkjet recording, which has characteristics of having a good hue as cyan ink, excellent fastnesses, in particular, extremely excellent water fastness when printed on plain paper, and high solubility in water or a water-soluble organic solvent.

18 Claims, No Drawings

U.S. PATENT DOCUMENTS

| | | |
|---|---|---|
| 2005/0126436 A1 | 6/2005 | Patel et al. |
| 2006/0201382 A1 | 9/2006 | Ozawa et al. |
| 2006/0268086 A1 | 11/2006 | Kawakami et al. |
| 2007/0006772 A1 | 1/2007 | Fujii et al. |
| 2008/0274286 A1 | 11/2008 | Yamashita et al. |
| 2009/0029120 A1 | 1/2009 | Fujii et al. |
| 2009/0047430 A1 | 2/2009 | Mori et al. |
| 2009/0151599 A1 | 6/2009 | Fujii et al. |
| 2009/0202798 A1 | 8/2009 | Patel |
| 2010/0112218 A1* | 5/2010 | Fujii et al. .................. 106/31.47 |
| 2010/0126377 A1* | 5/2010 | Yoneda et al. ............. 106/31.49 |
| 2010/0236448 A1* | 9/2010 | Kurata et al. ............. 106/31.49 |
| 2010/0279082 A1 | 11/2010 | Shimizu et al. |

FOREIGN PATENT DOCUMENTS

| | | |
|---|---|---|
| DE | 195 21 056 A1 | 12/1995 |
| EP | 0 418 792 A1 | 3/1991 |
| EP | 0 669 381 A2 | 8/1995 |
| EP | 0 906 943 A1 | 4/1999 |
| EP | 0 985 716 A1 | 3/2000 |
| EP | 1 741 756 A1 | 1/2007 |
| EP | 2028239 A1 | 2/2009 |
| GB | 2 290 548 A | 9/2010 |
| JP | 57-198758 A | 12/1982 |
| JP | 59-22967 A | 2/1984 |
| JP | 60-208365 A | 10/1985 |
| JP | 61-2772 A | 1/1986 |
| JP | 62-190273 A | 8/1987 |
| JP | 3-185080 A | 8/1991 |
| JP | 5-171085 A | 7/1993 |
| JP | 7-138511 A | 5/1995 |
| JP | 10-140063 A | 5/1998 |
| JP | 2000-303009 A | 10/2000 |
| JP | 2002-080762 A | 3/2002 |
| JP | 2002-105349 A | 4/2002 |
| JP | 2003-34758 A | 2/2003 |
| JP | 2004-075986 A | 3/2004 |
| JP | 2004-323605 A | 11/2004 |
| JP | 2006-45535 A | 2/2006 |
| JP | 2007-23251 A1 | 2/2007 |
| JP | 2007-277416 A | 10/2007 |
| JP | 2008-013706 A | 1/2008 |
| JP | 2009-057540 A | 3/2009 |
| JP | 2009-062515 A | 3/2009 |
| JP | 11-515048 A | 9/2010 |
| WO | 02/060994 A1 | 8/2002 |
| WO | 2004/087815 A1 | 10/2004 |
| WO | 2005/021658 A1 | 3/2005 |
| WO | 2007/091631 A1 | 8/2007 |
| WO | 2008/111635 A1 | 9/2007 |
| WO | 2007/116933 A1 | 10/2007 |
| WO | 2009/084195 A1 | 7/2009 |

OTHER PUBLICATIONS

XP-002435574; DataBase WPI Week 198608; Jan. 8, 1986; Derwent Publications Ltd.; Ink Composition Blue Colour Low Water Soluble comprise Sulphonated Copper Phthalo Cyanine Derivative Web Agent; 1-Page.

XP-002435575; DataBase WPI Week 198548; Oct. 19, 1985; Derwent Publications Ltd.; "Copper Phthalocyanine Compound Preparation React Chlorosulphonic Acid Ammonium Hydroxide Triazine Derivative"; 1-Page.

XP-002435576; DataBase WPI Week 198303; Dec. 6, 1982; Derwent Publications Ltd.; "Water Soluble Phthalocyanine Dye Low Affinity Cellulose Fast Washing Textile Print" 1-Page.

International Search Report dated May 15, 2007 in co-pending foreign application PCT/JP2007/052212.

International Search Report dated Apr. 22, 2008 in co-pending foreign application PCT/JP2008/054584.

International Search Report dated Sep. 15, 2009 in co-pending foreign application PCT/JP2009/002935.

* cited by examiner

PORPHYRAZINE COLORING MATTER AND INK COMPOSITION CONTAINING THE SAME

TECHNICAL FIELD

The present invention relates to a water-soluble porphyrazine coloring matter or a salt thereof, an ink composition containing this and a colored product colored therewith.

BACKGROUND ART

As for the recording method by means of an inkjet printer which is one of the typical methods among various color recording methods, various methods for discharging ink have been developed. In any of said discharging methods, ink droplets are generated and adhered onto various record-receiving materials (such as paper, film and cloth) to perform recording. This method has been rapidly prevailing lately and is expected to continue growing remarkably in the future because of features such as quietness without noise generation due to no direct contact of a recording head with a record-receiving material and as easiness in downsizing, speeding up and colorizing. Conventionally, as an ink for fountain pens, felt-tip pens or the like and as an ink for inkjet recording, inks where a water-soluble dye is dissolved in an aqueous medium have been used. In these water-based inks, a water-soluble organic solvent is generally added to prevent ink from clogging at a pen tip or an inkjet nozzle. These inks are required to provide recorded images with sufficient density, not to clog at a pen tip or a nozzle, to dry quickly on a record-receiving material, to bleed less, to have excellent storage stability, and so on. In addition, recorded images formed with said ink are required to have fastnesses such as water fastness, moisture fastness, light fastness and gas fastness.

Clogging at the nozzle of an inkjet is often due that water in an ink evaporates around the nozzle before the other solvent and additive do, resulting in the compositional condition that water remains less while the other solvent and additive remain more whereby the coloring matter solidifies and precipitates. Therefore, it is one of the very important performances required that solids hardly precipitate even when the ink is concentrated by evaporation of water from ink. For this reason, high solubility in solvents and additives is one of the properties required for coloring matters.

Meanwhile, in order that images or character information on a color display of a computer are recorded in color by an ink jet printer, subtractive color mixing of 4 color inks of yellow (Y), magenta (M), cyan (C) and black (K) is generally used, by which recorded images are expressed in color. In order that images by additive color mixing of red (R), green (G) and blue (B) on CRT (cathode ray tube) displays and the like are, as faithfully as possible, reproduced with images by subtractive color mixing, it is desired that coloring matters to be used for inks, particularly Y, M and C, have respectively a hue close to each standard and also are vivid. In addition, it is required that the inks are stable in storage for a long period of time, and that images printed have a high concentration and also the printed images are excellent in fastnesses as described above.

With the recent development of the inkjet techniques, improvement of printing speed in inkjet printing is remarkable. Consequently, there is a move to use an inkjet printer, as well as a laser printer using an electronic toner, for document printing on plain paper which is a major application in the office environment. The inkjet printer has some such advantages that there is no need to select the recording paper type and inkjet printers are comparatively inexpensive, and therefore it is becoming widespread particularly in small to medium scale office environments such as SOHO. When an inkjet printer is thus used for printing on plain paper, there is a tendency that hue and water fastness are more emphasized among the qualities required for printed matters. In order to satisfy these performances, a method using a pigment ink has been proposed. However, compared with dye ink, using pigment ink tends to cause such problems that the stability of the ink is poor and the nozzle of a printer head is clogged. In addition, when a pigment ink is used, the low abrasion resistance of printed images is often regarded as a problem, too. It is said that dye ink relatively hardly causes such problems that pigment ink does because dye as a coloring matter component is dissolved in ink. However, dye ink is significantly inferior in water fastness compared with pigment ink, whereby improvement thereof is strongly desired.

As a water-soluble cyan coloring matter used for an ink suitable for inkjet recording, phthalocyanine coloring matter and triphenylmethane-based coloring matter are representative. A typical phthalocyanine coloring matter which is the most widely reported and used includes phthalocyanine derivatives and the like classified into the following A to H.

A: Known phthalocyanine coloring matter such as known as color index C.I. numbers of Direct Blue 86, Direct Blue 87, Direct Blue 199, Acid Blue 249 or Reactive Blue 71 and the like.

B: Phthalocyanine coloring matter such as described in Patent Literatures 1 to 3 and the like [for example, a mixture of Cu-Pc-$(SO_3Na)_m(SO_2NH_2)_n$: m+n=1 to 4].

C: Phthalocyanine coloring matters described in Patent Literature 4 and the like [for example, Cu-Pc-$(CO2H)_m(CONR_1R_2)_n$: m+n=a number of 0 to 4].

D: Phthalocyanine coloring matter such as described in Patent Literature 5 and the like, [for example, Cu-Pc-$(SO_3H)_m(SO_2NR_1R_2)_n$: m+n=a number of 0 to 4 and m≠0].

E: Phthalocyanine coloring matter such as described in Patent Literature 6 and the like, [for example, Cu-Pc-$(SO_3H)_l(SO_2NH_2)_m(SO_2NR_1R_2)_n$: l+m+n=a number of 0 to 4].

F: Phthalocyanine coloring matter such as described in Patent Literature 7 and the like, [for example, Cu-Pc-$(SO_2NR_1R_2)_n$: n=a number of 1 to 5].

G: Phthalocyanine coloring matter such as described in Patent Literatures 8, 9, and 12 and the like, [a phthalocyanine compound where the substitution position of a substituent is controlled, and a phthalocyanine coloring matter where a substituent is introduced at the beta-position].

H: Benzopyridoporphyrazine-based coloring matter having a nitrogen-containing heterocyclic ring such as a pyridine ring, such as described in Patent Literatures 10, 13, 14 and 15 and the like.

In addition, many proposals have been made to the problem of improvement of water fastness on plain paper through the ages. As a blue coloring matter for inkjet which is excellent in water fastness and whose hue and light fastness are improved, for example, C.I.Direct Blue 86 and C.I.Direct Blue 199 described in Patent Literature 16 are proposed.

As for the dye described in Patent Literature 1, the water fastness thereof is excellent on certain kinds of plain paper but it cannot be said that it is excellent on various kinds of plain paper available on the market, whereby the applicable range is narrow. Therefore, a cyan coloring matter which has an excellent water fastness uniformly on more kinds of plain paper and is also excellent in light fastness, hue and color density has been required.

The Benzopyridoporphyrazine-based coloring matters having a nitrogen-containing heterocyclic ring and a benzene ring disclosed in Patent Literatures 10, 13, 14 and 15 and the like are ones to which active gas fastness, light fastness, moisture fastness, hue and the like are imparted, but improvement of water fastness on plain paper is not mentioned in any of them.

[Patent Literature 1]
JP 62-190273 A
[Patent Literature 2]
JP 7-138511 A
[Patent Literature 3]
JP 2002-105349 A
[Patent Literature 4]
JP 5-171085 A
[Patent Literature 5]
JP 10-140063 A
[Patent Literature 6]
JP 11-515048 A
[Patent Literature 7]
JP 59-22967 A
[Patent Literature 8]
JP 2000-303009 A
[Patent Literature 9]
JP 2002-249677 A
[Patent Literature 10]
JP 2003-34758 A
[Patent Literature 11]
JP 2002-80762 A
[Patent Literature 12]
WO 2004/087815
[Patent Literature 13]
WO 2002/034844
[Patent Literature 14]
JP 2004-75986 A
[Patent Literature 15]
WO 2007/116933 A
[Patent Literature 16]
JP 2001-294786 A

DISCLOSURE OF THE INVENTION

Problems to Be Solved by the Invention

It is an object of the present invention to provide a water-soluble cyan coloring matter which has a high solubility in water or a water-soluble organic solvent, hue and vividness suitable for inkjet recording and a high color density, and allows excellent fastnesses, such as light fastness, gas fastness, moisture fastness and water fastness, and particularly water fastness on various plain papers, of recorded matter, and to provide an ink composition containing it which has a good storage stability.

Means of Solving the Problems

The present inventors have intensively studied to solve the above problems and found that a water-soluble porphyrazine coloring matter represented by a particular formula or a salt thereof and an ink composition containing it can solve the above problems, and have completed the present invention.

That is, the present invention relates to:
(1) A porphyrazine coloring matter represented by the following formula (1) or a salt thereof:

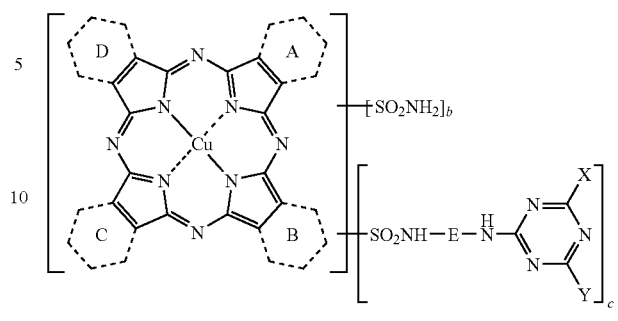

[wherein, the rings A, B, C and D shown by broken lines each independently represent a 6-membered ring having aromaticity, at least 1.0 of said four rings A to D is a benzene ring, and at least 0.5 of the rest is a nitrogen-containing heteroaromatic ring, when shown as an average value;

E represents an alkylene group;

X and Y are each independently an anilino group having 1 to 3 carboxy groups; and b is 0 to 3.4, c is 0.1 to 3.5, and the sum of b and c is 1.0 to 3.5, when shown as an average value], (2) The porphyrazine coloring matter or a salt thereof according to the above (1), wherein the nitrogen-containing heteroaromatic ring is a pyridine ring or a pyrazine ring, (3) The porphyrazine coloring matter or a salt thereof according to the above (1) or (2), which is obtained by reaction of a compound represented by the following formula (3) with an organic amine represented by the following formula (4) in the presence of ammonia:

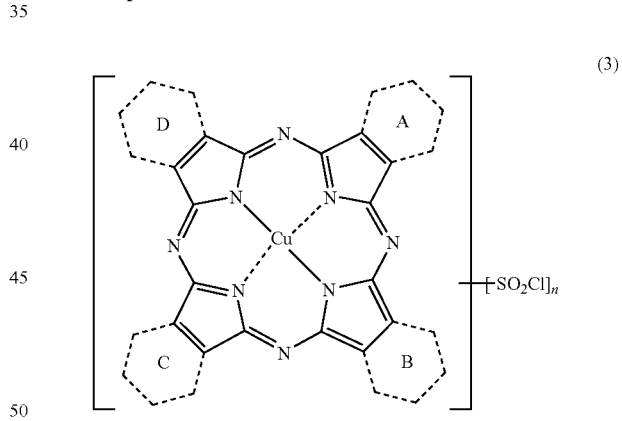

[wherein, the rings A, B, C and D shown by broken lines have the same meanings as those described in the above (1), and n is 1.0 to 3.5 when shown as an average value],

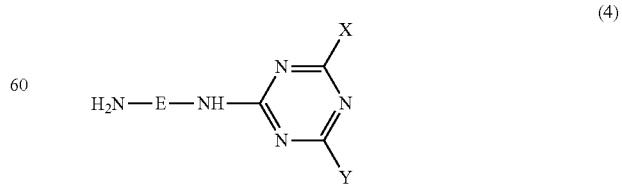

[wherein, E, X and Y have the same meanings as those described in the above (1)], (4) The porphyrazine coloring matter or a salt thereof according to the above (1) or (2), wherein 0.5 to 3.0 of the four rings A, B, C and D shown by broken lines is a pyridine ring or a pyrazine ring and 1.0 to 3.5 of the rest is a benzene ring, when shown as an average value;

E is a C2-C4 alkylene group;

X and Y are each independently an anilino group having 1 to 3 carboxy group; and b is 0 to 3.4, c is 0.1 to 3.5 and the sum of b and c is 1.0 to 3.5, when shown as an average value, (5) The porphyrazine coloring matter or a salt thereof according to the above (4), wherein E is an ethylene group or a propylene group, (6) The porphyrazine coloring matter or a salt thereof according to the above (1), wherein 0.5 to 3.0 of the four rings A, B, C and D shown by broken lines is a pyridine ring fused at the 2- and 3-positions or at the 3- and 4-positions, 1.0 to 3.5 of the rest is a benzene ring, when shown as an average value;

E is C2-C4 alkylene;

X and Y are each independently an anilino group having 1 to 3 carboxy groups;

b is 0 to 3.4, c is 0.1 to 3.5 and the sum of b and c is 1.0 to 3.5, when shown as an average value, (7) The porphyrazine coloring matter or a salt thereof according to the above (1) or (2) represented by the following formula (2):

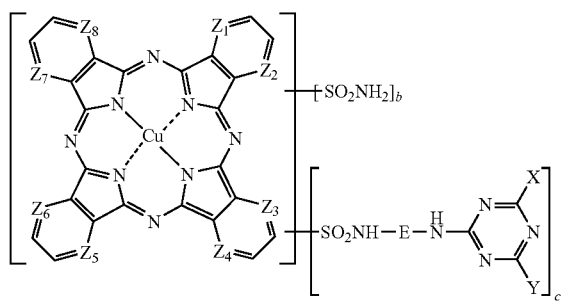

[wherein, $Z_1$ to $Z_8$ each independently represent a nitrogen atom or a carbon atom, at least 1.0 of the 4 combinations of $Z_1$ and $Z_2$, $Z_3$ and $Z_4$, $Z_5$ and $Z_6$, and, $Z_7$ and $Z_8$ is a combination of carbon atoms, at least 0.5 of the rest is a combination of a nitrogen atom and a carbon atom or a combination of nitrogen atoms, when shown as an average value;

E, X, Y, b and c have the same meanings as those of the above (1)], (8) The porphyrazine coloring matter or a salt thereof according to the above (7), which is obtained by reaction of a compound represented by the following formula (5) with an organic amine represented by the following formula (4) in the presence of ammonia:

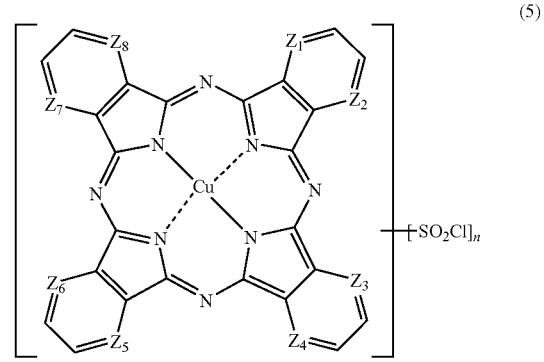

[wherein, $Z_1$ to $Z_8$ have the same meanings as those described in the above (7), and n is 1.0 to 3.5 when shown as an average value]

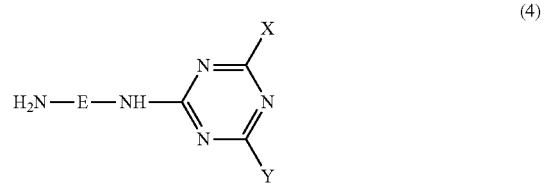

[wherein, E, X and Y have the same meanings as those described in the above (1)], (9) An ink composition characterized by containing, as a coloring matter component, the porphyrazine coloring matter according to any one of the above (1) to (8),

(10) The ink composition according to the above (9), which further contains a water-soluble organic solvent,

(11) The ink composition according to the above (9) or (10), which is for inkjet recording,

(12) A method for inkjet recording, characterized in that recording is performed on a record-receiving material by discharging an ink droplet of the ink according to any one of the above (9) to (11) responding to a recording signal,

(13) The method for inkjet recording according to the above (12), wherein the record-receiving material is a communication sheet,

(14) The method for inkjet recording according to the above (13), wherein the communication sheet is a surface treated sheet and has an ink image-receiving layer containing a white inorganic pigment particle on the support thereof,

(15) A container containing the ink composition according to any one of the above (9) to (11),

(16) An inkjet printer comprising the container according to the above (15),

(17) A colored product colored with the porphyrazine coloring matter according to any one of the above (1) to (8) or with the ink composition according to any one of the above (9) to (11).

Effect of the Invention

The water-soluble porphyrazine coloring matter represented by the above formula (1) of the present invention or a salt thereof has an excellent solubility in water and a water-soluble organic solvent. It has a characteristic of, for example, the good filterability through a membrane filter in the process of producing the ink composition and gives a very vivid hue of cyan color on inkjet recording paper. In addition, the ink composition of the present invention containing this compound has no crystal precipitation or no change in physical properties, hue and the like after storage for a long period of time, and thus the storage stability thereof is extremely good. And printed matter using the ink composition of the present invention as an ink for inkjet recording has an ideal hue as cyan color hue, without selecting a record-receiving material (for example, paper, film and the like), and it is also possible that photo-like color images are faithfully reproduced on paper.

In addition, the ink composition of the present invention has an extremely improved water fastness on plain paper, compared with conventional dye inks. Further, when recording is performed with said ink composition on a record-receiving material whose surface is coated with a porous white inorganic substance, such as inkjet special paper and film for photo image quality, the ink composition of the present invention has various good fastnesses, i.e. water fastness, moisture fastness, gas fastness and light fastness. Therefore, it allows excellent long-term storage stability of the photo-like recorded images. For these characteristics, said ink composition is very suitable for inkjet printing where no selection of recording media is one of its characteristics. As described above, the water-soluble porphyrazine coloring matter represented by the above formula (1) is thus extremely useful as a cyan coloring matter for ink, particularly for ink for inkjet recording.

BEST MODE FOR CARRYING OUT THE INVENTION

The present invention will be specifically explained. The porphyrazine coloring matter or a salt thereof of the present invention is represented by the above formula (1) or formula (2) and substantially a mixture of said porphyrazine coloring matter or a salt thereof. Hereinafter in the present description, "porphyrazine coloring matter or a salt thereof" of the present invention is merely described as "porphyrazine coloring matter" simplistically for convenience.

In addition, the superscript "®" represents a registered trademark in the present description.

In the above formula (1) or formula (3), the rings A, B, C and D shown by broken lines each independently represent a 6-membered ring (which is also referred to as aromatic 6-membered ring, hereinafter) having aromaticity, and at least 1.0 of said rings A to D is a benzene ring and at least 0.5 of them is a nitrogen-containing heteroaromatic ring, when shown as an average value.

The number of benzene rings or nitrogen-containing heteroaromatic rings in the rings A to D is represented by an average value of the number of benzene rings or nitrogen-containing heteroaromatic rings in the coloring matter represented by the above formula (1). That is, simply explained, for example, a coloring matter represented by the formula (1) where 3.5 are benzene rings and 0.5 is a nitrogen-containing heteroaromatic ring means that the half of all the coloring matter molecules is a compound where all of A to D are benzene rings and the rest half is a compound where one of A to D is a nitrogen-containing heteroaromatic ring on average, and in addition, for example, a coloring matter represented by the formula (1) where 2.5 are benzene rings and 1.5 are nitrogen-containing heteroaromatic rings means that the half of all the coloring matter molecules is a compound where 2 of A to D are benzene rings and the rest half is a compound where one of A to D is a nitrogen-containing heteroaromatic ring, on average. Therefore, when the number of nitrogen-containing heteroaromatic rings is 1 or less, the coloring matter represented by the above formula (1) contains both a coloring matter where at least one of the rings A to D is said nitrogen-containing heteroaromatic ring and a coloring matter where all of the rings A to D is a benzene ring. In this regard, the porphyrazine coloring matters of the present invention are not usually such simple mixtures having 2 components as described above, and the above values are average values of those mixtures.

Said nitrogen-containing heteroaromatic ring is preferably a nitrogen-containing heteroaromatic 6-membered ring containing 1 to 2 nitrogen atoms, including a pyridine ring, a pyrazine ring, a pyrimidine ring and a pyridazine ring, for example. Among them, preferable is a pyridine ring or a pyrazine ring and more preferable is a pyridine ring.

Among said four rings A, B, C and D, the preferable and specific number of the nitrogen-containing heteroaromatic ring is, when shown as an average value, usually 0.5 to 3.0, preferably 0.5 to 2.5 and more preferably 0.5 to 2.0, and the rest is a benzene ring. That is, the specific number of the benzene ring in this case is, when shown as an average value, usually 1.0 to 3.5, preferably 1.5 to 3.5 and more preferably 2.0 to 3.5.

The fused positions of said nitrogen-containing heteroaromatic ring may be any positions when plural two consecutive carbon atoms are present. For example, in the case of pyridine rings, they include the 2- and 3-positions or the 3- and 4-positions, and pyridine rings are preferably fused at the 2- and 3-positions. In the case of pyrazine rings, they are fused at the 2- and 3-positions.

As the number of said nitrogen-containing heteroaromatic rings increases, solubility in water, organic solvent and the like tends to decrease. For this reason, the number of nitrogen-containing heteroaromatic rings may be appropriately controlled considering water fastness and solubility to select a well-balanced ratio.

In the compound of the present invention, it is a preferable case that the number of nitrogen-containing heteroaromatic rings is, when shown as an average value, in the above range of said four rings A, B, C and D, and a more preferable case can include a case that the number of nitrogen-containing heteroaromatic rings is, when shown as an average value, 0.50 to 2.0 or 0.50 to 1.5 and in some instances 0.70 to 1.5, where the rest are benzene rings.

In the above formula (1), E represents an alkylene group. Said alkylene group may be any of straight-chain, branched-chain and cyclic alkylene, however, preferably straight-chain or cyclic and more preferably straight-chain. The number of carbon atoms is usually 2 to 12, preferably 2 to 6 and more preferably 2 to 4. Specific examples thereof includes straight-chain ones such as an ethylene group, a propylene group, a butylene group, a pentylene group and a hexylene group; cyclic ones such as cyclopropylenediyl, 1,2- or 1,3-cyclopentylenediyl and 1,2-, 1,3- or 1,4-cyclohexylenediyl; and the like. A preferable group as E is a C2-C4 alkylene group, more preferably an ethylene group, a propylene group and a butylene group, and further preferable is an ethylene group or a propylene group.

In the above formula (1), X and Y are each independently an anilino group having 1 to 3 carboxy groups. The number of carboxy groups on said anilino group is usually 1 to 3 and preferably 1 to 2. Specifically, X and Y are each independently, for example, an anilino group having a carboxy group, such as 2-carboxyanilino, 3-carboxyanilino and 4-carboxyanilino; an anilino group having 2 carboxy groups, such as 2,5-dicarboxyanilino and 3,5-dicarboxyanilino; an anilino group having 3 carboxy groups, such as 2,4,6-tricarboxyanilino; or the like. It is preferable that X and Y in the above formula (1) are each independently 3-carboxyanilino, 4-carboxyanilino or 3,5-dicarboxyanilino, and it is more preferable that the both are the same and any ones of them. It is further preferable that the both are 3-carboxyanilino.

In the above formula (1), b is 0 to 3.4, c is 0.1 to 3.5, and the sum of b and c is 1.0 to 3.5. b is preferably 0.5 to 3.0, more preferably 0.7 to 2.7, and further preferably 1 to 2.5, c is 0.5 to 2.5, more preferably 0.8 to 2.5, further preferably 0.8 to 2 and most preferably 0.8 to 1.7, and the sum of b and c is 1.0 to 3.5, preferably 1.5 to 3.5 and further preferably 2.0 to 3.5. For a more preferable ratio of b to c, b is 0.7 to 2.7, c is 0.8 to 1.7, and the sum of b and c is 1.5 to 3.5 and more preferably 2.0 to 3.5. As described later, the porphyrazine coloring matter of the present invention is produced as a mixture, so the numbers of said b and c are given when shown as an average value. As b is larger, ozone fastness tends to be improved, but bronzing tends to easily occur. The numbers of b and c may be appropriately controlled considering ozone fastness and bronzing property to select a well-balanced ratio.

The porphyrazine coloring matter of the present invention represented by the above formula (1) or (2) can be obtained by reaction of a compound represented by the above formula (3) or the formula (5) with an organic amine represented by the above formula (4) in the presence of ammonia. The reaction conditions and the like will be described later.

The porphyrazine coloring matter represented by the above formula (2) is preferable one among coloring matters represented by the above formula (1), and it is one where, in the case that the rings A to D shown by broken lines in the above formula (1) are nitrogen-containing heteroaromatic rings, the position of said nitrogen atom is identified. Specifically, the four rings containing $Z_1$ to $Z_8$ as ring-constituting atoms correspond to the four rings A to D shown by broken lines in the above formula (1).

In the formula (2), $Z_1$ to $Z_8$ each independently represent a nitrogen atom or a carbon atom (in the case of a carbon atom, said carbon atom has one hydrogen atom), and at least 1.0, as an average value, of four combinations of $Z_1$ and $Z_2$, $Z_3$ and $Z_4$, $Z_5$ and $Z_6$ and $Z_7$ and $Z_8$ is a combination of carbon atoms (specifically, a combination where the ring is a benzene ring) and at least 0.5 of the rest combinations is a combination where the ring is a nitrogen-containing aromatic ring, specifically, a combination of a nitrogen atom and a carbon atom or a combination of nitrogen atoms.

Therefore, the average values for the four combinations here have the same meanings as the average values of the numbers of nitrogen-containing heteroaromatic rings and benzene rings in the rings A to D of the formula (1) described above, and the preferable range is exactly the same.

More specifically, the preferable number of combinations where the ring is a nitrogen-containing heteroaromatic ring is, when shown as an average value, usually 0.5 to 3.0, preferably 0.5 to 2.5 and more preferably 0.5 to 2.0, and the rest are benzene rings. In addition, further preferable cases include a case where the number of combinations where the ring is a nitrogen-containing heteroaromatic ring is, when shown as an average value, 0.50 to 2.0 or 0.50 to 1.5, and in some instances, 0.70 to 1.5, where the rest are benzene rings.

Further, E, X, Y, b and c in the formula (2) are the same as in the above formula (1) respectively, including the preferable examples. In this regard, when any of $Z_1$ to $Z_8$ is a carbon atom, said carbon atom has one hydrogen atom.

The compound represented by free acid of the above formula (1) or formula (2) can also form a salt by using a carboxy group it has in its molecule. In the present invention, all compounds represented by the above formula (1) or formula (2) are, when they are represented in free acid form, included in the present invention, and compounds forming salts as the above are included in the present invention. Salts of the compound represented by the formula (1) or the formula (2) are preferably inorganic or organic cation salts. Examples of the salt include alkali metal salts, alkali earth metal salts and ammonium salts. Preferable alkali metal salts are salts of lithium, sodium and potassium.

Alkali earth metal for the alkali earth metal salt includes, for example, calcium, magnesium and the like.

The organic cation salt includes organic amine cation, specifically onium salts of organic amine. The said organic amine includes, for example, lower alkyl amines having 1 to 3 carbon atoms such as methylamine and ethylamine, and mono-, di- or tri(lower alkanol having 1 to 4 carbon atoms) amines such as monoethanolamine, diethanolamine, triethanolamine, monoisopropanolamine, diisopropanolamine and triisopropanolamine.

In addition, ammonium salt is included as another salt.

Among the above, preferable salts include alkali metal salts such as sodium salt, potassium salt and lithium salt; onium salts of mono-, di- or tri-(lower alkanol having 1 to 4 carbon atoms) amine such as monoethanolamine, diethanolamine, triethanolamine, monoisopropanolamine, diisopropanolamine and triisopropanolamine; and ammonium salts.

Specific examples of the rings A to D, E, X and Y in the porphyrazine coloring matter represented by the above formula (1) of the present invention will be shown in the following table 1, but the porphyrazine coloring matter of the present invention are not limited to the following examples. In addition, when the nitrogen-containing heteroaromatic rings corresponding to the rings A to D are pyridine rings, positional isomers for the nitrogen atom exist as described later. Therefore, some of these isomers are included and described in the following table 1. Further, many isomers exist even though they are not exemplified, and the present invention includes any of the isomers.

In this regard, as described later, positional isomers and other by-products other than main components come to be mixed in a coloring matter represented by the formula (1) of the present invention when it is synthesized, but they do not particularly cause any problems in the present invention even if it is used as it is.

TABLE 1

| No. | A | B | C | D | E | X | Y | b | c |
|---|---|---|---|---|---|---|---|---|---|
| 1 | 2,3-Pyrido | Benzo | Benzo | Benzo | Ethylene | 2-Carboxyanilino | 2-Carboxyanilino | 2 | 1 |
| 2 | 2,3-Pyrido | 2,3-Pyrido | Benzo | Benzo | Ethylene | 2-Carboxyanilino | 2-Carboxyanilino | 1 | 1 |
| 3 | 2,3-Pyrido | Benzo | 2,3-Pyrido | Benzo | Ethylene | 2-Carboxyanilino | 2-Carboxyanilino | 1 | 1 |
| 4 | 2,3-Pyrido | 2,3-Pyrido | 2,3-Pyrido | Benzo | Ethylene | 2-Carboxyanilino | 2-Carboxyanilino | 0 | 1 |
| 5 | 2,3-Pyrido | Benzo | Benzo | Benzo | Ethylene | 3-Carboxyanilino | 3-Carboxyanilino | 2 | 1 |
| 6 | 2,3-Pyrido | 2,3-Pyrido | Benzo | Benzo | Ethylene | 3-Carboxyanilino | 3-Carboxyanilino | 1 | 1 |
| 7 | 2,3-Pyrido | Benzo | 2,3-Pyrido | Benzo | Ethylene | 3-Carboxyanilino | 3-Carboxyanilino | 1 | 1 |
| 8 | 2,3-Pyrido | 2,3-Pyrido | 2,3-Pyrido | Benzo | Ethylene | 3-Carboxyanilino | 3-Carboxyanilino | 0 | 1 |

TABLE 1-continued

| No. | A | B | C | D | E | X | Y | b | c |
|---|---|---|---|---|---|---|---|---|---|
| 9 | 2,3-Pyrido | Benzo | Benzo | Benzo | Ethylene | 4-Carboxyanilino | 4-Carboxyanilino | 2 | 1 |
| 10 | 2,3-Pyrido | 2,3-Pyrido | Benzo | Benzo | Ethylene | 4-Carboxyanilino | 4-Carboxyanilino | 1 | 1 |
| 11 | 2,3-Pyrido | Benzo | 2,3-Pyrido | Benzo | Ethylene | 4-Carboxyanilino | 4-Carboxyanilino | 1 | 1 |
| 12 | 2,3-Pyrido | 2,3-Pyrido | 2,3-Pyrido | Benzo | Ethylene | 4-Carboxyanilino | 4-Carboxyanilino | 0 | 1 |
| 13 | 2,3-Pyrido | Benzo | Benzo | Benzo | Ethylene | 2,5-Dicarboxyanilino | 2,5-Dicarboxyanilino | 2 | 1 |
| 14 | 2,3-Pyrido | 2,3-Pyrido | Benzo | Benzo | Ethylene | 2,5-Dicarboxyanilino | 2,5-Dicarboxyanilino | 1 | 1 |
| 15 | 2,3-Pyrido | Benzo | 2,3-Pyrido | Benzo | Ethylene | 2,5-Dicarboxyanilino | 2,5-Dicarboxyanilino | 1 | 1 |
| 16 | 2,3-Pyrido | 2,3-Pyrido | 2,3-Pyrido | Benzo | Ethylene | 2,5-Dicarboxyanilino | 2,5-Dicarboxyanilino | 0 | 1 |
| 17 | 2,3-Pyrido | Benzo | Benzo | Benzo | Ethylene | 3,5-Dicarboxyanilino | 3,5-Dicarboxyanilino | 2 | 1 |
| 18 | 2,3-Pyrido | 2,3-Pyrido | Benzo | Benzo | Ethylene | 3,5-Dicarboxyanilino | 3,5-Dicarboxyanilino | 1 | 1 |
| 19 | 2,3-Pyrido | Benzo | 2,3-Pyrido | Benzo | Ethylene | 3,5-Dicarboxyanilino | 3,5-Dicarboxyanilino | 1 | 1 |
| 20 | 2,3-Pyrido | 2,3-Pyrido | 2,3-Pyrido | Benzo | Ethylene | 3,5-Dicarboxyanilino | 3,5-Dicarboxyanilino | 0 | 1 |
| 21 | 2,3-Pyrido | Benzo | Benzo | Benzo | Ethylene | 2,4,6-Tricarboxyanilino | 2,4,6-Tricarboxyanilino | 2 | 1 |
| 22 | 2,3-Pyrido | 2,3-Pyrido | Benzo | Benzo | Ethylene | 2,4,6-Tricarboxyanilino | 2,4,6-Tricarboxyanilino | 1 | 1 |
| 23 | 2,3-Pyrido | Benzo | 2,3-Pyrido | Benzo | Ethylene | 2,4,6-Tricarboxyanilino | 2,4,6-Tricarboxyanilino | 1 | 1 |
| 24 | 2,3-Pyrido | 2,3-Pyrido | 2,3-Pyrido | Benzo | Ethylene | 2,4,6-Tricarboxyanilino | 2,4,6-Tricarboxyanilino | 0 | 1 |
| 25 | 2,3-Pyrido | Benzo | Benzo | Benzo | Ethylene | 2-Carboxyanilino | 3-Carboxyanilino | 2 | 1 |
| 26 | 2,3-Pyrido | 2,3-Pyrido | Benzo | Benzo | Ethylene | 2-Carboxyanilino | 3-Carboxyanilino | 1 | 1 |
| 27 | 2,3-Pyrido | Benzo | 2,3-Pyrido | Benzo | Ethylene | 2-Carboxyanilino | 3-Carboxyanilino | 1 | 1 |
| 28 | 2,3-Pyrido | 2,3-Pyrido | 2,3-Pyrido | Benzo | Ethylene | 2-Carboxyanilino | 3-Carboxyanilino | 0 | 1 |
| 29 | 2,3-Pyrido | Benzo | Benzo | Benzo | Ethylene | 2-Carboxyanilino | 4-Carboxyanilino | 2 | 1 |
| 30 | 2,3-Pyrido | 2,3-Pyrido | Benzo | Benzo | Ethylene | 2-Carboxyanilino | 4-Carboxyanilino | 1 | 1 |
| 31 | 2,3-Pyrido | Benzo | 2,3-Pyrido | Benzo | Ethylene | 2-Carboxyanilino | 4-Carboxyanilino | 1 | 1 |
| 32 | 2,3-Pyrido | 2,3-Pyrido | 2,3-Pyrido | Benzo | Ethylene | 2-Carboxyanilino | 4-Carboxyanilino | 0 | 1 |
| 33 | 2,3-Pyrido | Benzo | Benzo | Benzo | Ethylene | 3-Carboxyanilino | 4-Carboxyanilino | 2 | 1 |
| 34 | 2,3-Pyrido | 2,3-Pyrido | Benzo | Benzo | Ethylene | 3-Carboxyanilino | 4-Carboxyanilino | 1 | 1 |
| 35 | 2,3-Pyrido | Benzo | 2,3-Pyrido | Benzo | Ethylene | 3-Carboxyanilino | 4-Carboxyanilino | 1 | 1 |
| 36 | 2,3-Pyrido | 2,3-Pyrido | 2,3-Pyrido | Benzo | Ethylene | 3-Carboxyanilino | 4-Carboxyanilino | 0 | 1 |
| 37 | 2,3-Pyrido | Benzo | Benzo | Benzo | Ethylene | 3-Carboxyanilino | 3,5-Dicarboxyanilino | 2 | 1 |
| 38 | 2,3-Pyrido | 2,3-Pyrido | Benzo | Benzo | Propylene | 3-Carboxyanilino | 3,5-Dicarboxyanilino | 1 | 1 |
| 39 | 2,3-Pyrido | Benzo | 2,3-Pyrido | Benzo | Butylene | 3-Carboxyanilino | 3,5-Dicarboxyanilino | 1 | 1 |
| 40 | 2,3-Pyrido | 2,3-Pyrido | 2,3-Pyrido | Benzo | Ethylene | 3-Carboxyanilino | 3,5-Dicarboxyanilino | 0 | 1 |
| 41 | 2,3-Pyrido | Benzo | Benzo | Benzo | Ethylene | 2,5-Dicarboxyanilino | 3,5-Dicarboxyanilino | 2 | 1 |
| 42 | 2,3-Pyrido | 2,3-Pyrido | Benzo | Benzo | Propylene | 2,5-Dicarboxyanilino | 3,5-Dicarboxyanilino | 1 | 1 |
| 43 | 2,3-Pyrido | Benzo | 2,3-Pyrido | Benzo | Butylene | 2,5-Dicarboxyanilino | 3,5-Dicarboxyanilino | 1 | 1 |
| 44 | 2,3-Pyrido | 2,3-Pyrido | 2,3-Pyrido | Benzo | Ethylene | 2,5-Dicarboxyanilino | 3,5-Dicarboxyanilino | 0 | 1 |
| 45 | 2,3-Pyrido | Benzo | Benzo | Benzo | Ethylene | 4-Carboxyanilino | 2,4,6-Tricarboxyanilino | 2 | 1 |
| 46 | 2,3-Pyrido | 2,3-Pyrido | Benzo | Benzo | Propylene | 4-Carboxyanilino | 2,4,6-Tricarboxyanilino | 1 | 1 |
| 47 | 2,3-Pyrido | Benzo | 2,3-Pyrido | Benzo | Butylene | 4-Carboxyanilino | 2,4,6-Tricarboxyanilino | 1 | 1 |
| 48 | 2,3-Pyrido | 2,3-Pyrido | 2,3-Pyrido | Benzo | Ethylene | 4-Carboxyanilino | 2,4,6-Tricarboxyanilino | 0 | 1 |
| 49 | 2,3-Pyrido | Benzo | Benzo | Benzo | Ethylene | 3,5-Dicarboxyanilino | 2,4,6-Tricarboxyanilino | 2 | 1 |
| 50 | 2,3-Pyrido | 2,3-Pyrido | Benzo | Benzo | Propylene | 3,5-Dicarboxyanilino | 2,4,6-Tricarboxyanilino | 1 | 1 |
| 51 | 2,3-Pyrido | Benzo | 2,3-Pyrido | Benzo | Butylene | 3,5-Dicarboxyanilino | 2,4,6-Tricarboxyanilino | 1 | 1 |
| 52 | 2,3-Pyrido | 2,3-Pyrido | 2,3-Pyrido | Benzo | Ethylene | 3,5-Dicarboxyanilino | 2,4,6-Tricarboxyanilino | 0 | 1 |

The method of producing the compound represented by the formula (1) of the present invention will be explained.

First, a compound represented by the following formula (6) is synthesized. The compound represented by the following formula (6) is obtained by, for example, reaction of a dicarboxylic acid derivative (which means dicarboxylic acid or a derivative thereof) of a 6-membered nitrogen-containing heteroaromatic ring having aromaticity with a phthalic acid derivative (which means phthalic acid or a derivative thereof) in the presence of a catalyst and a copper compound. It is possible to control the numbers of nitrogen-containing heteroaromatic rings and benzene rings in the rings A to D by changing the molar ratio in the reaction of said each derivative. For example, when a compound where 0.5 to 3.0 of the four aromatic 6-membered rings of A to D is a nitrogen-containing heteroaromatic ring and the rest are benzene rings is synthesized, an intended compound can be obtained by controlling the ratio so that the use ratio of a dicarboxylic acid derivative of the nitrogen-containing heteroaromatic ring is in the range of 0.125 to 0.75 mol, the use ratio of a phthalic acid derivative is in the range of 0.25 to 0.875 mol, and the total of the both is 1 mol. For example, in the case of one nitrogen-containing heteroaromatic ring and three benzene rings, a dicarboxylic acid derivative of a nitrogen-containing heteroaromatic ring may be used in an amount of 0.25 mol and a phthalic acid derivative may be used in an amount of 0.75 mol.

The dicarboxylic acid derivative of a nitrogen-containing heteroaromatic ring includes 6-membered ring dicarboxylic acid derivatives of a nitrogen-containing heteroaromatic ring respectively having a carboxy group or a reactive group (an acid amide group, an imide group, an acid anhydride group, a carbonitrile group and the like) derived from a carboxy group at the two adjacent positions, specifically dicarboxylic acid of a 6-membered nitrogen-containing heteroaromatic ring, and acid amide, acid imide, acid anhydride, carbonitrile or the like which are derived therefrom. More specifically, it includes dicarboxylic acid compounds such as quinolinic acid, 3,4-pyridinedicarboxylic acid and 2,3-pyrazinedicarboxylic acid; acid anhydride compounds such as quinolinic anhydride, 3,4-pyridinedicarboxylic anhydride and 2,3-pyrazinedicarboxylic anhydride; dicarboxyamide compounds such as pyridine-2,3-dicarboxyamide; dicarboxylic acid monoamide compounds such as pyrazine-2,3-dicarboxylic acid monoamide; acid imide compounds such as quinolinic acid imide; and dicarbonitrile compounds such as pyridine-2,3-dicarbonitrile and pyrazine-2,3-dicarbonitrile. In addition, specific examples of phthalic acid derivatives include phthalic acid, phthalic anhydride, phthalamide, phthalamic acid, phthalimide, phthalonitrile, 1,3-diiminoisoindoline and 2-cyanobenzamide, and the like.

The synthesis method of the compound represented by the following formula (6) include methods generally called nitrile method and Wyler method, and their reaction conditions and the like are different.

Nitrile method is a method using, as a raw material, a dicarbonitrile compound such as pyridine-2,3-dicarbonitrile, pyrazine-2,3-dicarbonitrile and phthalonitrile.

On the other hand, Wyler method uses, as a raw material, a dicarboxylic acid compound such as phthalic acid, quinolinic acid, 3,4-pyridinedicarboxylic acid and 2,3-pyrazinedicarboxylic acid; an acid anhydride compound such as phthalic anhydride, quinolinic anhydride, 3,4-pyridinedicarboxylic anhydride, 2,3-pyrazinedicarboxylic anhydride; a dicarboxyamide compound such as phthalic acid amide and pyridine-2,3-dicarboxyamide; a dicarboxylic acid monoamide compound such as phthalamic acid and pyrazine-2,3-dicarboxylic acid monoamide; an acid imide compound such as phthalic acid imide and quinolinic acid imide; and the like. In addition, in Wyler method, addition of urea is essential and the use amount of urea is 5 to 100 times molar quantity relative to the total 1 mol of a dicarboxylic acid derivative of a nitrogen-containing heteroaromatic ring and a phthalic acid derivative.

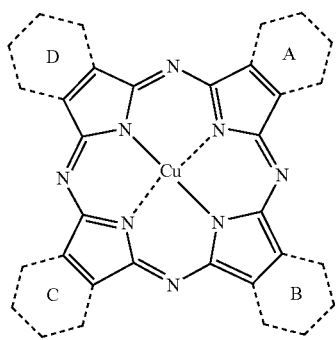

(6)

[wherein, the rings A, B, C and D have the same meanings as the above.]

Usually, the reaction is carried out in the presence of a solvent. As a solvent in nitrile method, an organic solvent having a boiling point of 100° C. or more and more preferably 130° C. or more is used. Specific examples of the solvent in nitrile method include n-amyl alcohol, n-hexanol, cyclohexanol, 2-methyl-1-pentanol, 1-heptanol, 1-octanol, 2-ethylhexanol, N,N-dimethylaminoethanol, benzyl alcohol, ethylene glycol, propylene glycol, trichlorobenzene, chloronaphthalene, nitrobenzene, quinoline, sulfolane, urea and the like.

On the other hand, as a solvent in Wyler method, an aprotic organic solvent having a boiling point of 150° C. or more and more preferably 180° C. or more is used. Specific examples of the solvent in Wyler method include trichlorobenzene, chloronaphthalene, nitrobenzene, quinoline, sulfolane, urea and the like. The use amount of the solvent is 1 to 100 times of the total mass of a dicarboxylic acid derivative of a nitrogen-containing heteroaromatic ring and a phthalic acid derivative. In this regard, even though urea is not an organic solvent and is a solid at room temperature, it can be preferably used as a solvent in the above reactions when reaction is carried out at 132° C. or higher because its melting point is 132° C.

The catalyst in nitrile method includes cyclic bases such as quinoline and 1,8-diazabicyclo[5,4,0]-7-undecene; amines such as tributylamine, ammonia and N,N-dimethylaminoethanol; alkali metal alcoholates such as sodium ethoxide and sodium methoxide; and the like. On the other hand, the catalyst in Wyler method includes ammonium molybdate, boric acid and the like. The addition amount of the catalyst is 0.001 to 1 time molar quantity relative to the total 1 mol of a dicarboxylic acid derivative of a nitrogen-containing heteroaromatic ring and a phthalic acid derivative.

The copper compound includes metal copper or copper compounds such as halide, carboxylate, sulfate, nitrate, acetylacetonate or complex of copper. Specific examples of these copper compounds include copper chloride, copper bromide, copper acetate, copper acetylacetonate and the like. The use amount of the copper compound is 0.15 to 0.35 time mol relative to the total 1 mol of dicarboxylic acid derivatives of a nitrogen-containing heteroaromatic ring and phthalic acid derivatives The reaction temperature in nitrile method is usually 100 to 200° C. and preferably 130 to 170° C. On the other hand, the reaction temperature in Wyler method is 150 to 300° C. and preferably 170 to 220° C. In addition, the reaction time varies depending on the reaction conditions but usually 1 to 40 hours. After completion of reaction, a compound represented by the above formula (6) is obtained by filtration, washing and drying.

The synthesis method will be more specifically explained taking, for example, a compound (copper dibenzobis(2,3-pyrido)porphyrazine) where two of the rings A to D represent pyridine rings and the rest two represent benzene rings in the above formula (6).

In a sulfolane solvent, quinolinic acid (0.5 mol), phthalic anhydride (0.5 mol), copper (II) chloride (0.25 mol), ammonium phosphomolybdate (0.004 mol) and urea (6 mol) are reacted at 200° C. for 5 hours, and thereby copper dibenzobis(2,3-pyrido)porphyrazine where two of the rings A to D represent pyridine rings and the rest two represent benzene rings in the above formula (6) is obtained.

In addition, when the synthesis is carried out by the above synthesis method, the main component of the product is copper dibenzobis(2,3-pyrido)porphyrazine and 5 kinds of isomers [the formulas (7-A) to (7-E) described later] where the positions of pyridine rings and the positions of nitrogen atoms of the pyridine rings are different is produced. In the same time, copper tribenzo(2,3-pyrido)porphyrazine [the formula (8) described later] where one of the rings A to D in the above formula (6) represents a pyridine ring and the rest three represent benzene rings and copper benzotris(2,3-pyrido)porphyrazine where three of the rings A to D in the above formula (6) represent pyridine rings and the rest one represents a benzene ring are by-produced. In said copper benzotris(2,3-pyrido)porphyrazine, positional isomers [the formula (9-A) to (9-D) described later] for nitrogen atoms of pyridine rings also exist and therefore the product is a complicated mixture. Further, copper tetrakis (2,3-pyrido)porphyrazine and copper phthalocyanine (copper tetrabenzoporphyrazine) are produced even though they are in a small amount, and thus the compound of the above formula (6) obtained by the above synthesis is substantially a mixture of plural compounds. Said mixture is used as copper dibenzobis(2,3-pyrido)porphyrazine, when shown as an average value, two of the rings A to D in the above mixture are pyridine rings and the rest two are benzene rings because it is difficult to isolate only an intended product from these mixtures. In this regard, the ratio of a nitrogen-containing heteroaromatic ring to a benzene ring where are contained in a compound the formula (6) can be determined by, for example, conducting analysis such as elemental analysis and the like.

Also in the case of a nitrogen-containing heteroaromatic ring where two of the rings A to D are not pyridine rings, for example, pyrazine rings, a compound where two of the rings A to D are nitrogen-containing heteroaromatic rings other than a pyridine ring such as pyrazine rings and the rest two are benzene rings can be obtained by synthesizing according to the above description using a corresponding dicarboxylic acid derivative of said nitrogen-containing heteroaromatic ring, such as 2,3-pyrazinedicarboxylic acid, instead of the above quinolinic acid. In addition, for a compound where the ratio thereof is different, such as a compound of the above formula (6) where 0.5 to 3.0 of the rings A to D is, when shown as an average value, a nitrogen-containing heteroaromatic ring and the rest are benzene rings, the use ratio of a dicarboxylic acid derivative and a phthalic acid derivative of a nitrogen-containing heteroaromatic ring is appropriately changed according to the ratio of a nitrogen-containing heteroaromatic ring to a benzene ring of an intended compound, and thereby said compound can be obtained in the same synthesis method as described above.

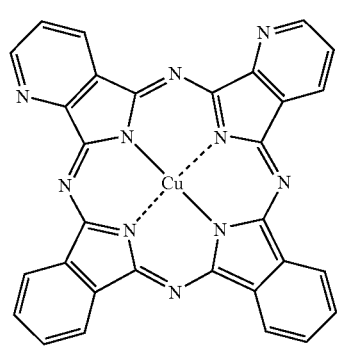

(7-A)

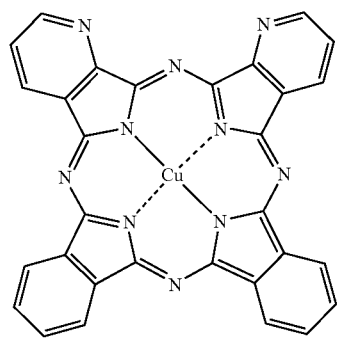

(7-B)

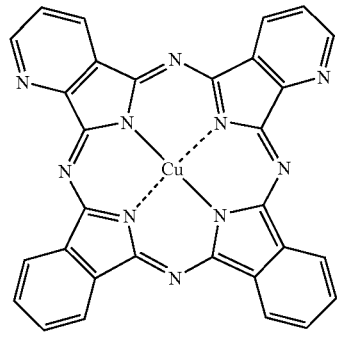

(7-C)

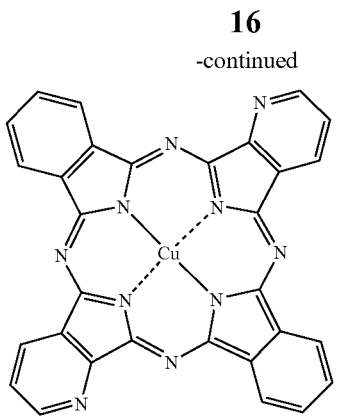

(7-D)

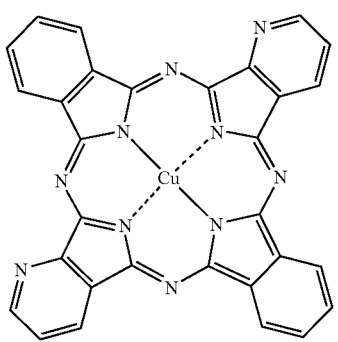

(7-E)

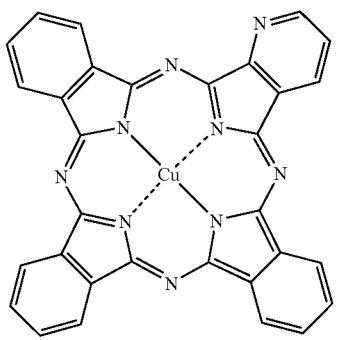

(8)

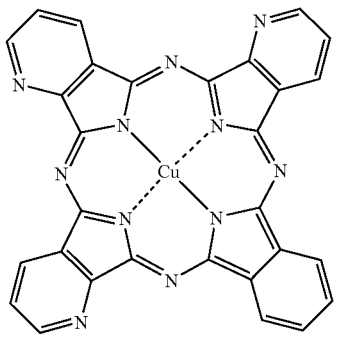

(9-A)

-continued

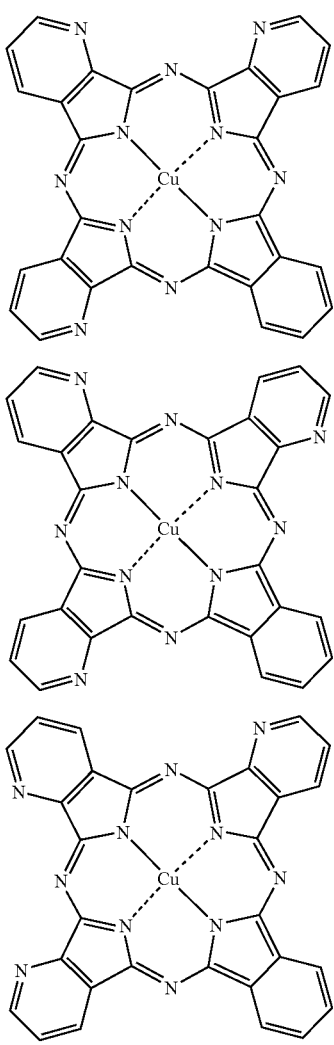

(9-B)

(9-C)

(9-D)

The compound represented by the above formula (3) or formula (5) can be obtained by chlorosulfonylation of a compound represented by the above formula (6) in chlorosulfonic acid. Otherwise, it can be also obtained by sulfonation of a compound represented by the above formula (6) in sulfuric acid or fuming sulfuric acid and then by conversion of the sulfo group to a chlorosulfonyl group with a chlorination agent. The chlorosulfonyl group or the sulfo group thus obtained is introduced not on a heteroaromatic ring group of the rings A to D but on a benzene ring of the rings A to D in the compound represented by the formula (6). Usually, one chlorosulfonyl group or one sulfo group is introduced on said benzene ring and therefore the number of these groups introduced is within the number of said benzene rings.

Therefore, the number (n) of $SO_2Cl$ in the compound of the formula (3) is 1.0 to 3.5 as an average value, corresponding to the number of benzene rings in the rings A to D of the compound of the formula (3). n in the formula (3) is preferably 1.5 to 3.5 and more preferably 2.0 to 3.5. n in the formula (5) is, as with that of the formula (3), 1.0 to 3.5, preferably 1.5 to 3.5 and more preferably 2.0 to 3.5, when shown as an average value.

By way of other synthesis examples of the compound represented by the above formula (3), it is also possible that a compound having a sulfo group represented by the following formula (10) is synthesized by cyclocondensation in advance using sulfo phthalic acid having a sulfo group and quinolinic acid, and then the sulfo group is converted to a chlorosulfonyl group to obtain an intended compound represented by the formula (3). The compound of the formula (5) can be also synthesized in the very same way by using a corresponding material compound.

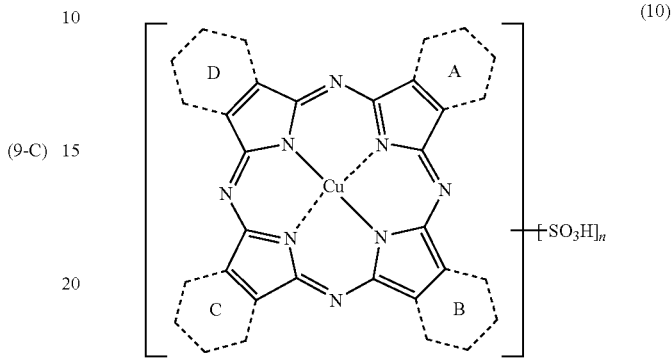

(10)

[Wherein, the rings A to D and n have the same meanings as in the above formula (3).]

The chlorosulfonylation of the compound of the above formula (6) is preferably carried out using chlorosulfonic acid as a solvent in an amount of usually 3 to 20 times by weight and preferably 5 to 10 times by weight of said compound. The reaction temperature is usually 100 to 150° C. and preferably 120 to 150° C. The reaction time varies according to the reaction conditions such as reaction temperature and usually 1 to 10 hours. Usually in this case, not all the substituents in a reaction product are chlorosulfonylated and some sulfo groups remain unreacted. It is preferred in the present invention that after the reaction with chlorosulfonic acid as a solvent, a chlorination agent such as thionyl chloride is further added to said solution and reaction is carried out in order that all the substituents are chlorosulfonylated. Said chlorination agent includes thionyl chloride, sulfuryl chloride, phosphorus trichloride, phosphorus pentachloride, phosphorous oxychloride and the like, but not limited thereto. The addition amount of the chlorination agent is 0.5 to 10 equivalents and about preferably 0.5 to 5 equivalents relative to the chlorosulfonyl group in an intended compound.

The conversion of a sulfo group in a sulfo-substituted copper porphyrazine coloring matter represented by the above formula (10) to a chlorosulfonyl group can be carried out by reaction of said compound with the above chlorination agent in the same way as described above. A reaction solvents to be used in said chlorination reaction includes sulfuric acid, fuming sulfuric acid, chlorosulfonic acid, benzene, toluene, nitrobenzene, chlorobenzene, N,N-dimethylformamide, N,N-dimethylacetoamide and the like, but not limited thereto.

Next, the compound represented by the above formula (3) and an organic amine represented by the above formula (4) are reacted in the presence of ammonia or an ammonia-producing compound (which are also altogether referred to as an aminating agent) in water solvent at usually pH 8 to 10 and 5 to 70° C. for 1 to 20 hours to obtain a porphyrazine coloring matter of the present invention represented by the above formula (1). As an aminating agent to be used in the reaction, ammonia or a compound producing ammonia (ammonia-producing compound) in the above reaction can be used, and it includes, for example, ammonium salt compounds such as ammonium chloride and ammonium sulfate; urea, ammonia water, ammonia gas and the like. However, it is not limited to these. In addition, said reaction is usually carried out in water solvent as described above.

In this regard, the use amount of an organic amine represented by the above formula (4) is usually 1 molar times or more of a theoretical value usually corresponding to c value relative to 1 mol of the compound represented by the above formula (3), but it varies according to reactivity of the organic amine and reaction conditions and is not limited thereto.

The values of b and c in the porphyrazine coloring matter of the present invention can be controlled by the use amount of the organic amine represented by the formula (4) in the synthesis reaction as described above. For example, in order to obtain a compound where b is 1.0, c is 1.5, and the sum of b and c is 2.5 in the formula (1), the above synthesis reaction is carried out using the organic amine represented by the formula (4) in an amount of 1.5 mol or a small excess thereof, relative to 1 mol of a compound where n is 2.5 in the formula (3). The products obtained by synthesis reaction of the compound represented by the formula (3) and the organic amine represented by the formula (4) are substantially mixtures of compounds having different values of b and c. Therefore, the values of b and c in the formula (1) and the formula (2) are average values of b and c in those mixtures.

The method of producing the organic amine represented by the above formula (4) will be explained. For example, 0.95 to 1.1 mol of carboxy-substituted aniline corresponding to X and 1 mol of 2,4,6-trichloro-S-triazine (cyanuric chloride) are reacted in water under conditions of usually pH 3 to 7 and 5 to 40° C. for 2 to 12 hours, to obtain a first condensate. Then, usually 0.95 to 1.5 mol of carboxy-substituted aniline corresponding to Y is added to the reaction liquid and the mixture is reacted under the conditions of pH 4 to 10 and 5 to 80° C. for 0.5 to 12 hours, and thereby a second condensate is obtained. Then, 1 to 50 mol of an alkylene diamine represented by the following formula (11) is added to the reaction liquid and the mixture is reacted under the conditions of usually pH 9 to 12 and 5 to 90° C. for 0.5 to 8 hours, and thereby a compound represented by the above formula (4) is obtained. Adjustment of the pH of the reaction liquid in each condensation reaction is carried out usually using an alkali metal hydroxide such as sodium hydroxide and potassium hydroxide or an alkali metal carbonate such as sodium carbonate and potassium carbonate. In this regard, the condensation order is appropriately determined according to reactivity of each compound and not limited to the above.

$$H_2N\text{-}E\text{-}NH_2 \qquad (11)$$

[wherein, E has the same meaning as in the above formula (1).]

In addition, the porphyrazine coloring matter of the present invention represented by the above formula (1) and (2) is synthesized by reaction of a compound represented by the above formula (3) or formula (5) with an organic amine represented by the above formula (4) in the presence of ammonia. This synthesis reaction does not require anhydrous conditions, so it is theoretically considered that a partial chlorosulfonyl compound represented by the formula (3) or the formula (5) is hydrolyzed with water existing within the reaction system and a compound converted to a sulfonic acid group is by-produced, and that said by-product comes to be mixed in an intended coloring matter represented by the formulas (1) and (2).

However, it is usually difficult to distinguish unsubstituted sulfamoyl groups from sulfonic acid groups by mass spectrometry to be used for analysis of reaction products. Therefore, in the present invention, all the chlorosulfonyl groups in the formula (3) or the formula (5) other than ones reacted with an organic amine represented by the formula (4) are described as ones converted to unsubstituted sulfamoyl groups.

In addition, as for the copper porphyrazine coloring matter represented by the above formulas (1) and (2), impurities where a copper porphyrazine ring (Pz) forms a dimer (for example, Pz-L-Pz) or a trimer via a divalent linking group (L) is occasionally by-produced and said by-product occasionally comes to be mixed in a reaction product.

The divalent linking group represented by the above L includes —$SO_2$—, —$SO_2$—NH—$SO_2$— and the like, and a by-product where these two Ls are combined is also occasionally formed in the case of the trimer.

The thus-obtained porphyrazine coloring matter of the present invention can be, according to necessity, separated by filtration and the like after aciding out or salting out. When salting out is carried out, it is preferably carried out in the range of, for example, acidic to alkaline pH and preferably pH 1 to 11. The temperature in the salting out is not particularly limited but usually 40 to 80° C. and preferably 50 to 70° C. More specifically, it is preferred that a reaction liquid containing a porphyrazine coloring matter of the present invention is heated to the above temperature and then sodium chloride, ammonium chloride and the like is added to adjust the pH in the above range for salting out.

The porphyrazine coloring matter of the present invention synthesized by the above method is obtained in free acid form or its salt form. In order to obtain it as free acid, for example, aciding out may be carried out. On the other hand, in order to obtain it as a salt, salting out may be carried out. When an intended salt is not obtained, a usual salt exchange method such as a method where a desired organic or inorganic base is, for example, added to one formed as free acid may be employed.

The porphyrazine coloring matter represented by the formulas (1) or (2) of the present invention is preferably one where:

0.5 to 3.0, more preferably 0.5 to 2.5 and further preferably 0.5 to 2.0 of the rings A to D are a pyridine ring or a pyrazine ring (more preferably, a pyridine ring), and 1.0 to 3.5, more preferably 1.5 to 3.5 and further preferably 2.0 to 3.5 of the rest is a benzene ring;

E is a C2 to C4 alkylene group and more preferably an ethylene group or a propylene group;

X and Y are independently an anilino group having 1 to 3 carboxy groups, more preferably an anilino group having 1 or 2 carboxy groups, further preferably 3-carboxyanilino, 4-carboxyanilino or 3,5-dicarboxyanilino and particularly preferably 3-carboxyanilino;

b is 0 to 3.4 and c is 0.1 to 3.5, and preferably b is 0.5 to 3.0 and c is 0.5 to 2.5, when shown as an average value;

the sum of b and c is 1.5 to 3.5, more preferably 2.0 to 3.5 and further preferably 2.5 to 3.5.

A combination of a more preferable one and another one among them is more preferably and a combination of 2 or 3 kinds of more preferable ones is further preferable.

Preferable porphyrazine coloring matters more specifically include as follows.

For example, they include:

(i) a porphyrazine coloring matter where 0.5 to 3.0 of the four rings of A, B, C and D shown by broken lines in the formula (1) or of the four rings containing $Z_1$ and $Z_2$, $Z_3$ and $Z_4$, $Z_5$ and $Z_6$ and $Z_7$ and $Z_8$ of the formula (2) is a pyridine ring or a pyrazine ring, and 1.0 to 3.5 of the rest is a benzene ring, when shown as an average value;

E is a C2-C4 alkylene group;

X and Y are each independently an anilino group having 1 to 3 carboxy groups;

b is 0 to 3.4 and optionally 0 to 3.2, c is 0.1 to 3.5 and optionally 0.1 to 3.3, and the sum of b and c is 1.0 to 3.5 and optionally 2.5 to 3.3, when shown as an average value, (ii) a porphyrazine coloring matter where 0.50 to 2.0, or 0.50 to 1.5 and optionally 0.70 to 1.5 of the four rings in the above (i) is a pyridine ring or a pyrazine ring, and the rest are benzene rings, when shown as an average value, and (iii) a porphyrazine coloring matter where X and Y in the above (i) or (ii) are each independently 3- or 4-carboxyanilino or 3,5-dicarboxyanilino.

Next, the ink composition of the present invention will be explained. The ink composition of the present invention is characterized by containing the porphyrazine coloring matter of the present invention. The porphyrazine coloring matter of the present invention produced by the above method exhibits vivid cyan. Therefore, an ink composition containing this is used as cyan ink. Said ink composition may be used as cyan ink (referred to as light cyan ink, photo cyan ink or the like) having a low concentration of coloring matter which is used to smoothly reproduce gradation part of images or to reduce granular appearance in hypochromic regions.

The ink composition of the present invention is prepared using water as a medium. When this ink composition is used as an ink for inkjet recording, the content of ions such as $Cl^-$ and $SO_4^{2-}$ contained as impurities in the porphyrazine coloring matter of the present invention is preferably less. Only as a guide for the content, the total content of $Cl^-$ and $SO_4^{2-}$ is 5% by mass or less, preferably 3% by mass or less and further preferably 1% by mass or less in the total mass of said coloring matter, and 1% by mass or less, preferably 0.5% or less and further preferably 0.1% or less in the total mass of an ink composition. The lower limit is not more than the detection limit of analysis equipment, and it may be specifically 0%. In order to produce a porphyrazine coloring matter of the present invention containing less $Cl^-$ and $SO_4^{2-}$, desalting treatment may be carried out by, for example, an ordinary method using a reverse osmosis membrane; a method where a dried form or a wet cake of said coloring matter is stirred in a mixed solvent of alcohol and water, filtered and dried; or the like. The alcohol to be used at this time is a lower alcohol having 1 to 4 carbon atoms, preferably an alcohol having 1 to 3 carbon atoms and further preferably methanol, ethanol or 2-propanol. In addition, a method where it is heated nearly to the boiling point of the alcohol to be used and then cooled for desalination in desalting treatment with alcohol can be also employed. The content of $Cl^-$ and $SO_4^{2-}$ can be measured by, for example, ion chromatography.

When the ink composition of the present invention is used as an ink for inkjet recording, it is preferred that a porphyrazine coloring matter of the present invention contained as a coloring matter in said ink composition to be used contains less heavy metal (ion) such as zinc and iron and less metal (ion) such as calcium and silica which are contained as impurities in the total mass of said coloring matter, except for copper (ion) contained as its central metal atom. The contents of heavy metal (ion) such as zinc and iron and metal (ion) such as calcium and silica are, for example, respectively about 500 ppm or less in a purified and dried form of the porphyrazine coloring matter of the present invention, only as a guide. The contents of heavy metal (ion) and metal (ion) are measured by ion chromatography, atomic absorption method and ICP (Inductively Coupled Plasma) emission spectrometry.

The ink composition of the present invention contains 0.1 to 8% by mass and preferably 0.3 to 6% by mass of a porphyrazine coloring matter of the present invention in the total mass, the rest is water, and it may also contain a water-soluble organic solvent and in addition, an additive (ink preparation agent) for ink as an optional component. It is preferred that the ink composition of the present invention further contains, according to necessity, a water-soluble organic solvent within the range not impairing the effects of the present invention, other than water. The water-soluble organic solvent is used for the purpose of function such as dye-dissolving, dry-preventing (wetting agent), viscosity-controlling, penetration-enhancing, surface tension-controlling and antifoaming. It may further contain, as other ink preparation agents, additives such as, for example, an antiseptic and fungicide, a pH adjuster, a chelating agent, a rust preventive agent, an ultraviolet absorbing agent, a viscosity modifier, a dye-dissolving agent, an antifading agent, an emulsion stabilizer, a surface tension modifier, an antifoaming agent, a dispersing agent and a dispersion stabilizer. Said ink composition preferably contains 0 to 60% by mass, preferably 5 to 50% and more preferably 10 to 50% by mass of a water-soluble organic solvent and 0 to 20% by mass and preferably 0 to 15% by mass of an ink preparation agent relative to the total amount of the ink composition. The rest is water.

A water-soluble organic solvent to be used in the present invention includes, for example, C1-C4 alkanols such as methanol, ethanol, n-propanol, isopropanol, n-butanol, isobutanol, secondary butanol and tertiary butanol; carboxylic acid amides such as N,N-dimethylformamide or N,N-dimethylacetoamide; heterocyclic ketones such as 2-pyrrolidone, N-methyl-2-pyrrolidone, 1,3-dimethylimidazolidin-2-one or 1,3-dimethylhexahydropyrimid-2-one; ketones or keto alcohols such as acetone, methyl ethyl ketone and 2-methyl-2-hydroxypentan-4-one; cyclic ethers such as tetrahydrofuran and dioxane; mono-, oligo- or poly-alkylene glycols or thioglycols having a C2-C6 alkylene unit such as ethylene glycol, 1,2-or 1,3-propylene glycol, 1,2-or 1,4-butylene glycol, 1,6-hexylene glycol, diethylene glycol, triethylene glycol, tetraethylene glycol, dipropylene glycol, thiodiglycol, polyethylene glycol and polypropylene glycol; polyols (preferably C3-C6 triol) such as glycerine and hexane-1,2,6-triol; C1-C4 monoalkyl ethers of polyhydric alcohol such as ethylene glycol monomethyl ether or ethylene glycol monoethyl ether, diethylene glycol monomethyl ether, diethylene glycol monoethyl ether, diethylene glycol monobutyl ether, triethylene glycol monomethyl ether, triethylene glycol monoethyl ether; and in addition, gamma-butyrolactone or dimethylsulfoxide and the like.

Preferable water-soluble organic solvents in the ink composition of the present invention are isopropanol, glycerine, mono, di- or tri-ethylene glycol, dipropylene glycol, 2-pyrrolidone, N-methyl-2-pyrrolidone and butyl carbitol and more preferably isopropanol, glycerine, diethylene glycol, N-methyl-2-pyrrolidone and butyl carbitol. These water-soluble organic solvents are used alone or as a mixture thereof.

The antiseptic and fungicide includes, for example, compounds of organic sulfur-based, organic nitrogen sulfur-based, organic halogen-based, haloallylsulfone-based, iodopropargyl-based, N-haloalkylthio-based, benzothiazole-based, nitrile-based, pyridine-based, 8-oxyquinoline-based, isothiazoline-based, dithiol-based, pyridineoxide-based, nitropropane-based, organic tin-based, phenol-based, quaternary ammonium salt-based, triazine-based, thiadiazine-based, an ilide-based, adamantane-based, dithiocarbamate-based, brominated indanone-based, benzyl bromoacetate-based, inorganic salt-based and the like.

The organic halogen-based compound includes, for example, sodium pentachlorophenol.

The pyridineoxide-based compound includes, for example, sodium 2-pyridinethiol-1-oxide.

The isothiazoline-based compound includes, for example, 1,2-benzisothiazolin-3-one, 2-n-octyl-4-isothiazolin-3-one, 5-chloro-2-methyl-4-isothiazolin-3-one, 5-chloro-2-methyl-4-isothiazolin-3-one magnesium chloride, 5-chloro-2-methyl-4-isothiazolin-3-one calcium chloride, 2-methyl-4-isothiazolin-3-one calcium chloride and the like.

In addition, other antiseptic and fungicides include sodium acetate, sodium sorbate, sodium benzoate and the like (for example, trade name: Proxel® GXL(S), Proxel® XL-2(S) and the like, manufactured by Avecia Corp.).

As the pH adjuster, any substance can be used as long as it can control the pH of ink in the range of 6.0 to 11.0 for the purpose of improving storage stability of ink. Examples thereof include alkanolamines such as diethanolamine and triethanolamine; alkali metal hydroxides such as lithium hydroxide, sodium hydroxide, potassium hydroxide; ammonium hydroxide; alkali metal carbonates such as lithium carbonate, sodium carbonate and potassium carbonate; and the like.

The chelating agent includes, for example, sodium ethylenediaminetetraacetate, sodium nitrilotriacetate, sodium hydroxyethylethylenediaminetriacetate, sodium diethylenetriaminepentaacetate, sodium uracildiacetate and the like.

The rust preventive agent includes, for example, hydrogen sulfite salt, sodium thiosulfate, ammonium thioglycolate, diisopropylammonium nitrite, pentaerythritol tetranitrate, dicyclohexylammonium nitrite and the like.

The ultraviolet absorbing agent includes, for example, benzophenone-based compounds, benzotriazole-based compounds, cinnamic acid-based compounds, triazine-based compounds, stilbene-based compounds or the like. In addition, a compound absorbing ultraviolet rays and emitting fluorescence as typified by a benzoxazole-based compound, so-called fluorescent brightening agent, can be also used.

The viscosity modifier includes water-soluble polymer compounds other than a water-soluble organic solvent, including, for example, polyvinyl alcohol, cellulose derivatives, polyamine, polyimine and the like.

The dye-dissolving agent includes, for example, urea, epsilon-caprolactam, ethylene carbonate and the like.

The antifading agent is used for the purpose of improving storage stability of images. As the antifading agent, various organic-based and metal complex-based antifading agents can be used. The organic antifading agent includes hydroquinones, alkoxyphenols, dialkoxyphenols, phenols, anilines, amines, indanes, chromans, alkoxyanilines, hetero ring compounds and the like, and the metal complex includes nickel complex, zinc complex and the like.

The surface tension modifier includes surfactants, for example, anionic surfactants, amphoteric surfactants, cationic surfactants, nonionic surfactants and the like.

The anionic surfactant includes alkyl sulfo carboxylate, alpha-olefin sulfonate, polyoxyethylene alkyl ether acetate, N-acylamino acid or a salt thereof, N-acylmethyltaurine salt, alkylsulfate polyoxyalkyl ether sulfate, alkylsulfate polyoxyethylene alkyl ether phosphate, rosin acid soap, castor oil sulfate, lauryl alcohol sulfate, alkyl phenol-type phosphoric acid ester, alkyl-type phosphoric acid ester, alkylaryl sulfonate, diethyl sulfosuccinate, diethylhexyl sulfosuccinate, dioctylsulfosuccinate and the like.

The cationic surfactant includes 2-vinylpyridine derivatives, poly(4-vinylpyridine) derivatives and the like.

The amphoteric surfactant includes lauryldimethylaminoacetic acid betaine, 2-alkyl-N-carboxymethyl-N-hydroxyethyl imidazolinium betaine, coconut oil fatty acid amide propyldimethylaminoacetic acid betaine, polyoctylpolyaminoethylglycine, imidazoline derivatives and the like.

The nonionic surfactant includes ether-based ones such as polyoxyethylene nonylphenyl ether, polyoxyethylene octylphenyl ether, polyoxyethylene dodecylphenyl ether, polyoxyethylene oleyl ether, polyoxyethylene lauryl ether and polyoxyethylene alkyl ether; ester-based ones such as polyoxyethylene oleate ester, polyoxyethylene distearate ester, sorbitan laurate, sorbitan monostearate, sorbitan monooleate, sorbitan sesquioleate, polyoxyethylene monooleate and polyoxyethylene stearate; acetylene glycol (alcohol)-based ones such as 2,4,7,9-tetramethyl-5-decyne-4,7-diol, 3,6-dimethyl-4-octyne-3,6-diol and 3,5-dimethyl-1-hexyn-3-ol; and the like. Other specific examples thereof include, for example, Surfynol® 104, 82 and 465, and Olfine STG (which are all manufactured by Nissin Chemical Industry Co., Ltd.) and the like.

As the antifoaming agent, a highly oxidized oil-based, glycerin fatty acid ester-based, fluorine-based or silicone based compound is used according to necessity.

These ink preparation agents are used alone or as a mixture thereof. In this regard, the surface tension of the ink composition of the present invention is usually 25 to 70 mN/m and more preferably 25 to 60 mN/m. In addition, the viscosity of the ink of the present invention is preferably 30 mPa·s or less and it is more preferably adjusted to 20 mPa·s or less.

In preparation of the ink composition of the present invention, the dissolving order of agents is not particularly limited. Water to be used in preparation of the ink composition is preferably water containing less impurity, such as ion-exchanged water or distilled water. In addition, microfiltration may be carried out using a membrane filter according to necessity to remove foreign substances, and it is preferred to carry out microfiltration when the ink composition of the present invention is used as an ink for inkjet printers. The pore size of a filter to be used for microfiltration is usually 1 μm to 0.1 μm and preferably 0.8 μm to 0.1 μm.

The ink composition of the present invention can be used not only for monochrome image formation but also for full color image formation. In order to form full color images, it is used together with magenta ink and yellow ink in an ink set of 3 primary colors and further in a 4 color ink set where black ink is added to this. In order to further form higher resolution images, it is also used in an ink set where light magenta ink, blue ink, green ink, orange ink, dark yellow ink, gray ink and the like are used in combination When the ink composition of the present invention is used in the above ink sets, various coloring matters can be used as a coloring matter of yellow ink. For example, its coupling component (hereinafter, referred to as coupler component) includes aryl or heteroarylazo dyes having a heterocycle, such as phenols, naphthols, anilines, pyrazolone and pyridone; azomethine dyes; methine dyes such as benzylidene dye and monomethine oxonol dye; quinone-based dyes such as naphthoquinone dye and anthraquinone dye; and the like, and in addition to these dye species, it can include quinophthalone dyes; nitro-nitroso dyes; acridine dyes; acridinone dyes; and the like.

Likewise, as a coloring matter of magenta ink, various ones can be used. It can include condensed polycyclic dyes such as aryl or heteroarylazo dyes having, as its coupler component, for example, phenols, naphthols, anilines and the like; azomethine dyes having, as its coupler component, for example, pyrazolones, pyrazolotriazoles and the like; methine dyes such as, for example, arylidene dye, styryl dye, merocyanine dye, cyanine dye and oxonol dye; carbonium dyes such as diphenyl methane dye, triphenylmethane dye and xanthene dye; quinone dyes such as naphthoquinone, anthraquinone and anthrapyridone; dioxazine dyes; and the like.

Likewise, the black coloring matter can include azo-based dyes such as disazo, trisazo and tetraazo, and in addition, carbon black dispersions.

The ink composition of the present invention can be used for recording methods such as impress printing, copying, marking, writing, drafting and stamping, and is particularly suitable for use in inkjet recording.

The inkjet recording method of the present invention is a method where the ink composition prepared as described above is filled in an ink container and said ink composition is discharged as ink droplets by supplying said ink composition with energy to form images on a known record-receiving material, for example plain paper, resin-coated paper, inkjet special paper, glossy paper, glossy film, electrophotography paper, fiber and cloth (such as cellulose and nylon, wool), glass, metal, ceramics, leather and the like.

In order to record on a record-receiving material by the inkjet recording method of the present invention, for example, a container (also referred to as ink tank and the like) containing the above ink is installed in a predetermined position of an inkjet printer and recording is performed on a record-receiving material in an ordinary manner. The inkjet printer includes, for example, piezo type printers utilizing mechanical vibration, bubble jet® type printers utilizing bubbles generated by heating, and the like.

In forming images, a polymer particle dispersion (also referred to as polymeric latex) may be also used in combination for the purpose of imparting glossiness and water fastness and of improving weatherability. The timing of providing polymeric latex to a record-receiving material may be before, after or at the same time as providing colorant. Therefore, according to the recording method of the present invention, polymeric latex may be added to a record-receiving material or the ink, and also may be, as a single liquid, applied to a record-receiving material.

The colored product of the present invention is a product colored with the porphyrazine coloring matter of the present invention or the ink composition of the present invention containing this on a color-receiving material using an inkjet printer or the like. The color-receiving material is not particularly limited and may be any of the record-receiving materials described above and, in addition, any other article as long as they can be colored by an inkjet printer. The color-receiving material includes, for example, communication sheets such as paper and film, fiber and cloth (such as cellulose nylon and wool), leather, substrates for color filters, and the like. The communication sheet is preferably one subjected to surface treatment, and specifically one provided with an ink-receiving layer of a substrate such as paper, synthetic paper and film. Said ink-receiving layer is provided by, for example, impregnating or coating a substrate as described above with a cation polymer, or by coating a surface of substrate as described above with an inorganic particle which can absorb coloring matter in ink, such as porous silica, aluminasol and special ceramics, together with a hydrophilic polymer such as polyvinyl alcohol and polyvinylpyrrolidone. Such communication sheet provided with an ink-receiving layer is usually called inkjet special paper (film), glossy paper (film) and the like.

The plain paper refers to a paper not particularly provided with any ink-receiving layer and a number of various kinds thereof are commercially available according to application. By way of example of the commercially available plain paper, one for inkjet includes both sides-high quality plain paper manufactured by Seiko-Epson Corporation; color plain paper manufactured by Canon Inc.; and Multipurpose Paper and All-in-one Printing Paper manufactured by Hewlett Packard; and the like. In addition to these, PPC paper which is not limited to application of inkjet printing is also plain paper.

The ink composition of the present invention is particularly excellent in water fastness on plain paper as described above, and for this reason, it is suitably used for plain paper in particular. In addition, it is excellent in fastness against light, ozone, humidity, friction and the like. It is excellent in water fastness on inkjet special paper, special film, glossy paper, glossy film or the like which are provided with an ink-receiving layer for inkjet printing, and also excellent in light fastness, ozone fastness, moisture fastness, abrasion resistance and the like on their communication sheet.

The ink according to the present invention is free from precipitation and separation during storage. In addition, when an ink according to the present invention is used for inkjet recording, it is also free from clogging an injector (inkhead). The ink according to the present invention shows no change in physical properties in use under constant circulation for a relatively long time by a continuous ink jet printer or in intermittent use by an on-demand inkjet printer.

The ink of the present invention is vivid cyan and can provide recorded matter particularly excellent in water fastness and also excellent in light fastness and ozone fastness. By using it in a set of cyan inks having different concentrations and also by using it together with other inks of yellow, magenta and in addition according to necessity, green, red, orange, blue and the like which are excellent in water fastness, light fastness and ozone fastness, color tone in a wide visible region can be expressed and recorded matter particularly excellent in water fastness and also excellent in light fastness and ozone fastness can be obtained.

EXAMPLES

Hereinafter, the present invention will be more specifically explained with reference to the examples. All the operations such as synthesis reaction and purification by suspension are carried out under stirring unless otherwise specifically noted. In addition, all the porphyrazine coloring matters of the present invention synthesized in the examples are mixtures as described above. Further, when the rings A to D in the structural formulas in the examples are pyridine rings, said pyridine rings are fused at the 2- and 3-positions. Furthermore, "part(s)" and "%" in the examples are based on mass unless otherwise specifically described. Moreover, for each compound whose maximum absorption wavelength ($\lambda$max) was measured, its measured value is denoted together with the measurement solvent.

In this regard, all the synthesized porphyrazine coloring matters of the present invention had a solubility of 100 g/L or more in water.

Example 1

(1) Synthesis of a compound of the above formula (6) where, 1.5 of the rings A to D are pyridine rings and 2.5 of them are benzene rings, when shown as an average value.

To a four-neck flask, 250 parts of sulfolane, 18.4 parts of phthalimide, 12.5 parts of quinolinic acid, 72.0 parts of urea, 8.8 parts of copper chloride (II) dihydrate (purity: 97.0%) and 1.0 part of ammonium molybdate were added, the liquid temperature was raised to 200° C., and the liquid was maintained at the same temperature for 5 hours to carry out the reaction. After completion of the reaction, the reaction liquid was cooled to 65° C., 200 parts of methanol were added thereto, and the precipitated solid was separated by filtration. The resulting solid was washed with 150 parts of methanol followed by 200 parts of hot water to obtain 72.2 parts of a wet cake. After the whole volume of the obtained wet cake was added to 500 parts of 5% hydrochloric acid, the liquid temperature was raised to 60° C. and the liquid was maintained at the same temperature for 1 hour. Under room temperature, the precipitated solid was separated by filtration and washed with 200 parts of water to obtain a wet cake. The whole volume of the obtained wet cake was added to 500 parts of 10% ammonia water and said liquid was maintained at 60° C. for 1 hour. The precipitated solid was separated by filtration and the resulting solid was sequentially washed with 300 parts of water and 100 parts of methanol to obtain 33.6 parts of a wet cake. The obtained wet cake was dried at 80° C. to obtain 19.8 parts of an intended compound as a blue solid.

λmax: 663.5 nm (in pyridine)

(2) Synthesis of a compound of the above formula (3) where, 1.5 of the rings A to D are pyridine rings, 2.5 of them are benzene rings, and n is 2.5, when shown as an average value.

After 5.8 parts of the compound obtained in Example 1 (1) were gradually added to 46.2 parts of chlorosulfonic acid while maintaining the temperature at 60° C. or less, the liquid temperature was raised to 140° C. and the liquid was reacted at this temperature for 4 hours. The reaction liquid was cooled to 70° C., 17.9 parts of thionyl chloride were added dropwise to the reaction liquid over 30 minutes, and the reaction was carried out at the same temperature for 3 hours. The reaction liquid was cooled to 30° C. or less and slowly poured in 800 parts of ice water. The precipitated solid was separated by filtration and washed with 200 parts of cold water to obtain 40.0 parts of a wet cake of an intended compound.

(3) Synthesis of a compound represented by the following formula (12) [the formula (4) where X and Y are 3-carboxyanilino and E is ethylene].

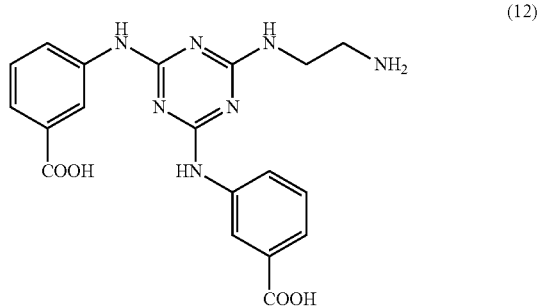

(12)

To 150 parts of ice water, 18.4 parts of cyanuric chloride and 0.2 parts of LEOCOL® TD-90 (surfactant manufactured by Lion Corporation) were added, and the mixture was stirred at 10° C. or less for 30 minutes. Next, 28.0 parts of 3-carboxy aniline (purity: 99%) were added thereto and the reaction was carried out at 0 to 10° C. for 1 hour 30 minutes, at 20 to 25° C. for 1 hour 30 minutes and at 40 to 45° C. for 1 hour 30 minutes while maintaining the pH at 6.0 to 7.0 with a 10% aqueous sodium hydroxide solution. To the reaction liquid, 60 parts of ethylenediamine were added dropwise, the reaction was carried out at room temperature overnight, and then the reaction liquid was adjusted to pH 5.0 with concentrated hydrochloric acid. At this time, the total amount of the reaction liquid was 1000 parts. To this reaction liquid, 100 parts of sodium chloride was added, the mixture was stirred for 30 minutes, and the precipitated solid was separated by filtration to obtain 207.5 parts of a wet cake. After 600 parts of water were added to the obtained wet cake, the pH was adjusted to 9.0 with a 10% aqueous sodium hydroxide solution. At this time, the total amount of the solution was 850 parts. This solution was adjusted to pH 5.0 with concentrated hydrochloric acid and stirred for 30 minutes to precipitate a solid. The precipitated solid was separated by filtration and washed with 200 parts of water to obtain 221 parts of a wet cake. The obtained wet cake was dried to obtain 40.1 parts of white powder of an intended compound of the above formula (12).

(4) Synthesis of a porphyrazine coloring matter of the present invention represented by the following formula (13) [the above formula (1) where 1.5 of the rings A to D are pyridine rings and 2.5 of them are benzene rings when shown as an average value, E is ethylene, and X and Y are 3-carboxyanilino].

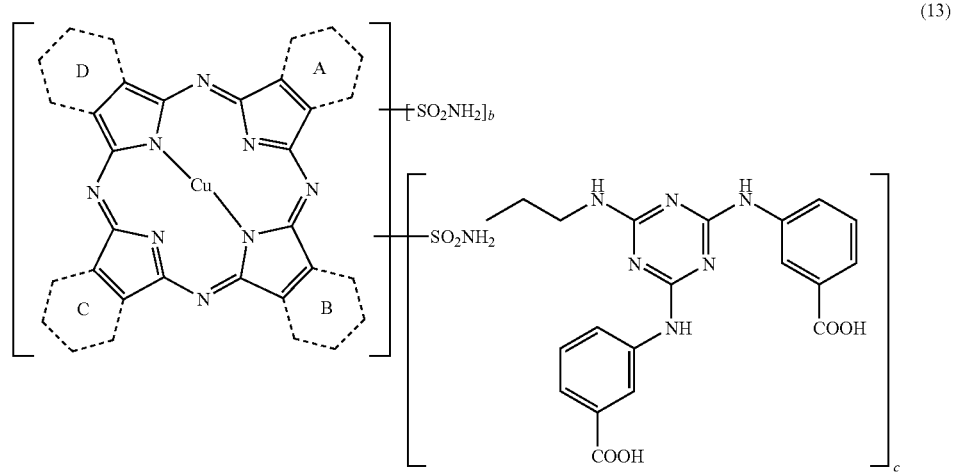

(13)

To 100 parts of ice water, 40.0 parts of the wet cake of the compound obtained in the above (2) in the present example, and this suspension was stirred at 5° C. or less. After 10 minutes, both 2.5 parts of 28% ammonia water and a solution dissolving 6.2 parts of the compound of the above formula (12) in 60 parts of water were added to this suspension while maintaining the liquid temperature at 10° C. or less, and then 28% ammonia water was further added there to adjust the pH to 9.0. The liquid temperature was raised to 20° C. over 1 hour while maintaining the same pH by appropriately adding the same ammonia water, the same temperature was maintained for 8 hours to carry out the reaction. At this time, the total amount of the reaction liquid was 230 parts. The reaction liquid was raised to 50° C. and adjusted to pH 3.0 over 20 minutes with concentrated hydrochloric acid. The resulting precipitate was separated by filtration and washed with 200 parts of water to obtain 56.0 parts of a wet cake. The obtained wet cake was dried to obtain 11.8 parts of free acid of an intended porphyrazine coloring matter (coloring matter where b is 1.24 and c is 1.26) of the present invention represented by the above formula (13) as blue powder.

λmax: 610.5 nm (in aqueous solution)

C. for 1 hour 30 minutes, at 20 to 25° C. for 1 hour 30 minutes and at 40 to 45° C. for 1 hour 30 minutes while adjusting the pH to 6.0 to 7.0 with a 10% aqueous sodium hydroxide solution. To the reaction liquid, 60 parts of ethylenediamine were added dropwise, the mixture was stirred at room temperature overnight, and then the pH was adjusted to 5.0 with concentrated hydrochloric acid. At this time, the total amount of the reaction liquid was 1000 parts. To this reaction liquid, 100 parts of sodium chloride were added, the mixture was stirred for 30 minutes, and the precipitated solid was separated by filtration to obtain 405.5 parts of a wet cake. After 600 parts of water were added to the obtained wet cake, the pH was adjusted to 9.0 with a 10% aqueous sodium hydroxide solution to give a solution. At this time, the total amount of the solution was 900 parts. This solution was adjusted to pH 5.0 with concentrated hydrochloric acid and stirred for 30 minutes, and the precipitated solid was separated by filtration. The resulting solid was washed with 200 parts of water to obtain 189.7 parts of a wet cake. The obtained wet cake was dried to obtain 39.2 parts of white powder of an intended compound represented by the above formula (14).

(2) Synthesis of a porphyrazine coloring matter of the present invention represented by the following formula (15) [the above formula (1) where 1.5 of the rings A to D are pyridine rings and 2.5 of them are benzene rings when shown as an average value, E is ethylene, and X and Y are 4-carboxyanilino].

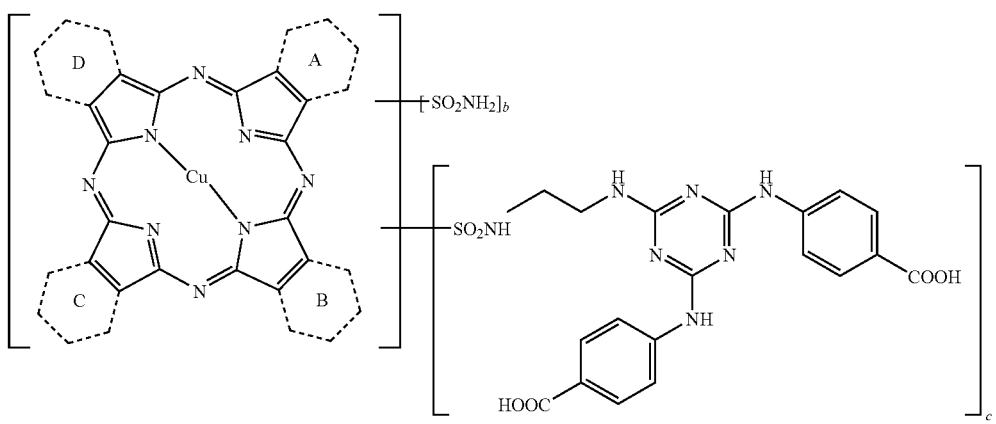

(15)

Example 2

(1) Synthesis of a compound represented by the following formula (14) [the formula (4) where X and Y are 4-carboxyanilino and E is ethylene].

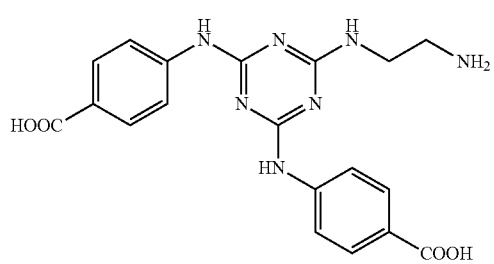

(14)

To 150 parts of ice water, 18.4 parts of cyanuric chloride and 0.2 parts of LEOCOL® TD-90 (surfactant) were added, and the mixture was stirred at 10° C. or less for 30 minutes. Next, 28.0 parts of 4-carboxy aniline (purity: 99%) were added to this, and then the reaction was carried out at 0 to 10°

To 100 parts of ice water, 40.0 parts of a wet cake (wet cake of a compound of the above formula (3) where 1.5 of the rings A to D are pyridine rings and 2.5 of them are benzene rings when shown as an average value, and n is 2.5) obtained in the same manner as that of Example 1 (2) were added, and this suspension was stirred at 5° C. or less. After 10 minutes, both 2.5 parts of 28% ammonia water and a solution dissolving 6.2 parts of a compound represented by the above formula (15) in 60 parts of water were added to this suspension while maintaining the liquid temperature at 10° C. or less. Further, 28% ammonia water was added there to adjust the pH to 9.0. The liquid temperature was raised to 20° C. over 1 hour while maintaining the same pH by appropriately adding the same ammonia water, and the liquid was maintained at the same temperature for 8 hours to carry out the reaction. At this time, the total amount of the reaction liquid was 230 parts. The liquid temperature of the reaction liquid was raised to 50° C., and the reaction liquid was adjusted to pH 3.0 over 20 minutes with concentrated hydrochloric acid. The precipitated solid was separated by filtration and washed with 200 parts of water to obtain 62.0 parts of a wet cake. The obtained wet cake was dried to obtain 13.0 parts of free acid of an intended porphyrazine coloring matter (coloring matter where b is 1.06 and c is 1.49) of the present invention represented by the above formula (15) as blue powder.

λmax: 610.5 nm (in aqueous solution)

Example 3

(1) Synthesis of a compound represented by the following formula (16) [the formula (4) where X and Y are 3,5-dicarboxyanilino, and E is ethylene].

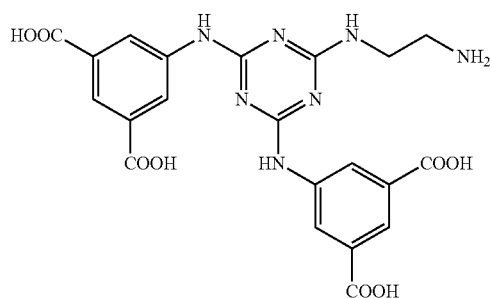

(16)

To 330 parts of ice water, 18.4 parts of cyanuric chloride and 0.2 parts LEOCOL® TD-90 (surfactant) were added, and the mixture was stirred at 10° C. or less for 30 minutes. Next, 36.3 parts of 3,5-dicarboxyaniline (purity: 99.3%) were added to this, and the reaction was carried out at 0 to 5° C. for 1 hour and subsequently at 25 to 30° C. for 3 hours while adjusting the pH to 7.0 to 7.5 with a 10% aqueous sodium hydroxide solution and further reacted at 40 to 45° C. for 1 hour while adjusting to pH 8.0 to 8.5. To the reaction liquid, 60 parts of ethylenediamine were added dropwise, the reaction liquid was stirred at room temperature overnight and then adjusted to pH 4.0 with concentrated hydrochloric acid, and said reaction liquid was stirred for 30 minutes. The precipitated solid was separated by filtration to obtain 400.1 parts of a wet cake. To the obtained wet cake, 280 parts of water were added, and the pH was adjusted to 9.0 with a 10% aqueous sodium hydroxide solution to give a solution. At this time, the total amount of the solution was 800 parts. This solution was adjusted to pH 5.0 with concentrated hydrochloric acid and stirred for 30 minutes. The precipitated solid was separated by filtration and washed with 200 parts of water to obtain 189.7 parts of a wet cake. The obtained wet cake was dried to obtain 50.2 parts of white powder of an intended compound represented by the above formula (16).

(2) Synthesis of a porphyrazine coloring matter of the present invention represented by the following formula (17) [the above formula (1) where 1.5 of the rings A to D are pyridine rings and 2.5 of them are benzene rings, E is ethylene, and X and Y are 3,5-dicarboxyanilino].

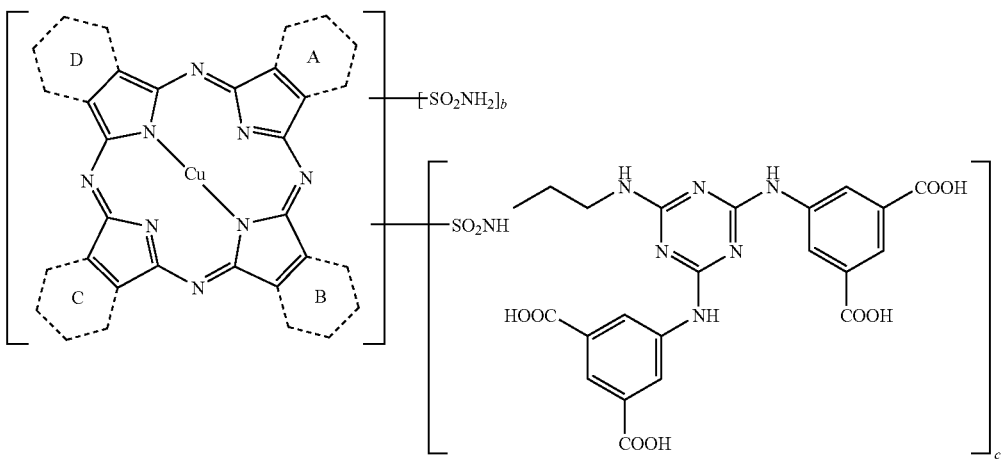

(17)

To 100 parts of ice water, 40.0 parts of a wet cake obtained in the same manner as that of Example 1 (2) were added, and this suspension was stirred at 5° C. or less. After 10 minutes, both 2.5 parts of 28% ammonia water and a solution dissolving 7.6 parts of a compound represented by the formula (21) in 60 parts of water were added to this suspension while maintaining the liquid temperature at 10° C. or less, and then further 28% ammonia water was added there to adjust the pH to 9.0. The liquid temperature was raised to 20° C. over 1 hour while maintaining the same pH by appropriately adding the same ammonia water, and the reaction liquid was maintained at the same temperature for 8 hours. At this time, the total amount of the reaction liquid was 230 parts. The liquid temperature of the reaction liquid was raised to 50° C., and the reaction liquid was adjusted to pH 4.0 over 20 minutes with concentrated hydrochloric acid. The precipitated solid was separated by filtration and washed with 200 parts of water to obtain 124.1 parts of a wet cake. The obtained wet cake was dried to obtain 26.6 parts of free acid of an intended porphyrazine coloring matter of the present invention represented by the above formula (17) as blue powder.

λmax: 603.5 nm (in aqueous solution)

Example 4

(1) Synthesis of a compound represented by the above formula (6) where 1.0 of the rings A to D is a pyridine ring and 3.0 of them are benzene rings when shown as an average value.

After 250 parts of sulfolane, 22.1 parts of phthalimide, 8.36 parts of quinolinic acid, 72.0 parts of urea, 8.8 parts of copper chloride (II) dihydrate (purity: 97.0%) and 1.0 part of ammonium molybdate were added to a four-neck flask, the liquid temperature was raised to 200° C. and the reaction liquid was maintained at the same temperature for 5 hours. After completion of the reaction, the reaction liquid was cooled to 65° C., 200 parts of methanol were added there, and the precipitated solid was separated by filtration. The obtained solid was sequentially washed with 150 parts of methanol and with 200 parts of hot water to obtain 74.2 parts of a wet cake. After the whole volume of the obtained wet cake was added to 500 parts of 5% hydrochloric acid, the liquid temperature was raised to 60° C. and said reaction liquid was maintained at the same temperature for 1 hour. The precipitated solid was separated by filtration and washed with 200 parts of water to obtain a wet cake. After the whole volume of the obtained wet cake was added to 500 parts of 10% ammonia water, said reaction liquid was maintained at 60° C. for 1 hour. The precipitated solid was separated by filtration and sequentially washed with 300 parts of water and with 100 parts of methanol to obtain 36.6 parts of a wet cake. The wet cake was dried at 80° C. to obtain 21.8 parts of an intended compound as a blue solid.

λmax: 655.0 nm (in pyridine)

(2) Synthesis of a compound of the above formula (3) where 1.0 of the rings A to D is a pyridine ring, 3.0 of them are benzene rings, and n is 3.0, when shown as an average value.

After 5.8 parts of the compound obtained in (1) of the present example were gradually added to 46.2 parts of chlorosulfonic acid while maintaining the liquid temperature at 60° C. or less, the liquid temperature was raised to 140° C. and the liquid was reacted for 4 hours reaction. The reaction liquid was cooled to 70° C., 17.9 parts of thionyl chloride were added dropwise to the reaction liquid over 30 minutes, and the reaction was carried out at the same temperature for 3 hours. The reaction liquid was cooled to 30° C. or less and slowly poured into 800 parts of ice water. The precipitated solid was separated by filtration and washed with 200 parts of cold water to obtain 41.0 parts of a wet cake of an intended compound.

(3) Synthesis of a porphyrazine coloring matter of the present invention represented by the above formula (13) [the above formula (1) where 1.0 of the rings A to D is a pyridine ring and 3.0 of them are benzene rings when shown as an average value, E is ethylene, and X and Y are 3-carboxyanilino].

To 100 parts of ice water, 41.0 parts of the wet cake obtained in (2) of the present example were added, and this suspension was stirred at 5° C. or less. After 10 minutes, 2.5 parts of 28% ammonia water and a solution dissolving 5.2 parts of a compound represented by the above formula (12) obtained in the same manner as that of Example 1 (3) in 60 parts of water were added while maintaining the liquid temperature at 10° C. or less, and further 28% ammonia water was added to adjust the pH to 9.0. The liquid temperature was raised to 20° C. over 1 hour while maintaining the same pH by appropriately adding the same ammonia water, and the reaction liquid was maintained at the same temperature for 8 hours. At this time, the total amount of the reaction liquid was 230 parts. After the liquid temperature of the reaction liquid was raised to 50° C. and the reaction liquid was adjusted to pH 2.0 over 20 minutes with concentrated hydrochloric acid, the precipitated solid was separated by filtration and washed with 200 parts of water to obtain 55.0 parts of a wet cake. The obtained wet cake was dried to obtain 10.8 parts of free acid of an intended porphyrazine coloring matter (coloring matter where b is 2.08 and c is 0.92) of the present invention represented by the above formula (13) as blue powder.

λmax: 611.0 nm (in aqueous solution)

Example 5

(1) Synthesis of a compound represented by the above formula (6) where 0.75 of the rings A to D is a pyridine ring and 3.25 of them are benzene rings when shown as an average value.

After 250 parts of sulfolane, 23.9 parts of phthalimide, 6.27 parts of quinolinic acid, 72.0 parts of urea, 8.8 parts of copper chloride (II) dihydrate (purity: 97.0%) and 1.0 parts of ammonium molybdate were added to a four-neck flask, the liquid temperature was raised to 200° C. and the reaction liquid was reacted at the same temperature for 5 hours. After completion of the reaction, the liquid temperature was cooled to 65° C., 200 parts of methanol was added to the reaction liquid, and the precipitated solid was separated by filtration. The resulting solid was sequentially washed with 150 parts of methanol and with 200 parts of hot water to obtain 78.3 parts of a wet cake. After the whole volume of the obtained wet cake was added to 500 parts of 5% hydrochloric acid, the liquid temperature was raised to 60° C. and the reaction liquid was maintained at the same temperature for 1 hour. The precipitated solid was separated by filtration and washed with 200 parts of water to obtain a wet cake. After the whole volume of the obtained wet cake was added to 500 parts of 10% ammonia water, the liquid temperature was raised to 60° C. and the reaction liquid was maintained at the same temperature for 1 hour. The precipitated solid was separated by filtration and then sequentially washed with 300 parts of water and with 100 parts of methanol to obtain 39.4 parts of a wet cake. The obtained wet cake was dried at 80° C. to obtain 24.3 parts of an intended compound as a blue solid.

(2) Synthesis of a compound of the above formula (3) where 0.75 of the rings A to D is a pyridine ring, 3.25 of them are benzene rings, and n is 3.25, when shown as an average value.

To 46.2 parts of chlorosulfonic acid, 5.8 parts of the compound obtained in (1) of the present example were gradually added while maintaining the liquid temperature at 60° C. or less. After that, the liquid temperature was raised to 140° C. and the reaction was carried out for 4 hours. The reaction liquid was cooled to 70° C., 17.9 parts of thionyl chloride were added dropwise to the reaction liquid over 30 minutes, and the reaction was carried out at the same temperature for 3 hours. The reaction liquid was cooled to 30° C. or less and slowly poured into 800 parts of ice water. The precipitated solid was separated by filtration and washed with 200 parts of cold water to obtain 43.3 parts of an intended compound.

(3) Synthesis of a porphyrazine coloring matter of the present invention represented by the above formula (13) [the above formula (1) where 0.75 of the rings A to D is a pyridine ring and 3.25 of them is benzene rings when shown as an average value, E is ethylene, and X and Y are 3-carboxyanilino].

To 100 parts of ice water, 43.3 parts of the wet cake of the compound obtained in (2) of the present example were added, and this suspension was stirred at 5° C. or less. After 10 minutes, 2.5 parts of 28% ammonia water and a solution dissolving 4.1 parts of the compound represented by the above formula (12) obtained in the same manner as that of Example 1 (3) in 60 parts of water were added while maintaining the liquid temperature at 10° C. or less, and then further, 28% ammonia water was added there to adjust the pH to 9.0. The liquid temperature was raised to 20° C. over 1 hour while maintaining the same pH by appropriately adding the same ammonia water, and the same temperature was maintained for 8 hours to carry out the reaction. At this time, the total amount of the reaction liquid was 240 parts. The liquid temperature of the reaction liquid was raised to 50° C. and the reaction liquid was adjusted to pH 2.0 over 20 minutes with concentrated hydrochloric acid. The precipitated solid was separated by filtration and then washed with 200 parts of water to obtain 92.0 parts of a wet cake. The obtained wet cake was dried to obtain 11.9 parts of free acid of an intended porphyrazine coloring matter (coloring matter where b is 2.29 and c is 0.96) of the present invention represented by the above formula (13) as blue powder.

λmax: 611.5 nm (in aqueous solution)

Evaluation Test (A) Preparation of Ink

Examples 6 to 10

Using the porphyrazine coloring matter of the present invention obtained in the above Example 1 as a coloring matter, the components were mixed according to the composition ratio shown in the following table 2 to give an ink composition of the present invention, which was then filtered through a 0.45 μm membrane filter for removing foreign substances to prepare an ink for inkjet recording for evaluation test. This ink preparation is Example 6. In this regard, ion-exchanged water was used as water, and an aqueous ammonia solution and water were added so that the pH of the ink composition was 9.5 and the total amount was 100 parts.

Further, in the same manner as that of Example 6 except that the coloring matters obtained in Examples 2 to 5 were used instead of the porphyrazine coloring matter of the present invention obtained in Example 1, inks were prepared. These ink preparations are Examples 7 to 10, respectively.

TABLE 2

| (Composition ratio of the ink composition) | |
|---|---|
| The porphyrazine coloring matter obtained in Example 1 | 5.0 parts |
| Glycerine | 5.0 parts |
| Urea | 5.0 parts |
| N-Methyl-2-pyrrolidone | 4.0 parts |
| Isopropylalcohol | 3.0 parts |
| Butyl carbitol | 2.0 parts |
| Trade name: Surfynol$^{RTM}$ 104PG50(note) | 0.1 part |
| Ammonia water + water | 75.9 parts |
| Total | 100.0 parts |

(Note):
An acetylene glycol nonionic surfactant manufactured by Nissin Chemical Industry Co., Ltd.

Comparative Example 1

In the same manner as that of Example 1 except that a coloring matter (C.I.Direct Blue 86) represented by the following formula (18) was used as a coloring matter instead of the porphyrazine coloring matter of the present invention obtained in Example 1, an ink of Comparative Example 1 was prepared.

In this regard, the sulfonic acid group in said coloring matter is a mixture of groups substituted at the 3-position of the phthalocyanine, and the formula (18) shown below is one of the structural formulas to be assumed. In addition, it is known that this coloring matter is a sodium salt.

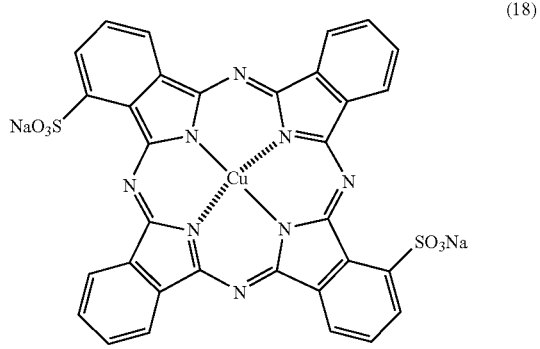

(18)

Comparative Example 2

A sodium salt of the coloring matter used in Comparative Example 1 was converted to an ammonium salt according to a conventional method. In the same manner as that of Example 1 except that the ammonium salt of the coloring matter of Comparative Example 1 obtained by the above salt exchange was used as a coloring matter instead of the porphyrazine coloring matter of the present invention obtained in Example 1, an ink of Comparative Example 2 was prepared, Comparative Example 3

In the same manner as that of Example 1 except that a coloring matter described in Example 3 (2) of Patent Literature 15 represented by the following formula (19) was used as a coloring matter instead of the porphyrazine coloring matter of the present invention obtained in Example 1, an ink of Comparative Example 3 was prepared.

In this regard, in the following formula (19), 1.5 of the four 6-membered aromatic rings A to D are pyridine rings which are fused at the 2- and 3-positions, and the rest 2.5 are benzene rings.

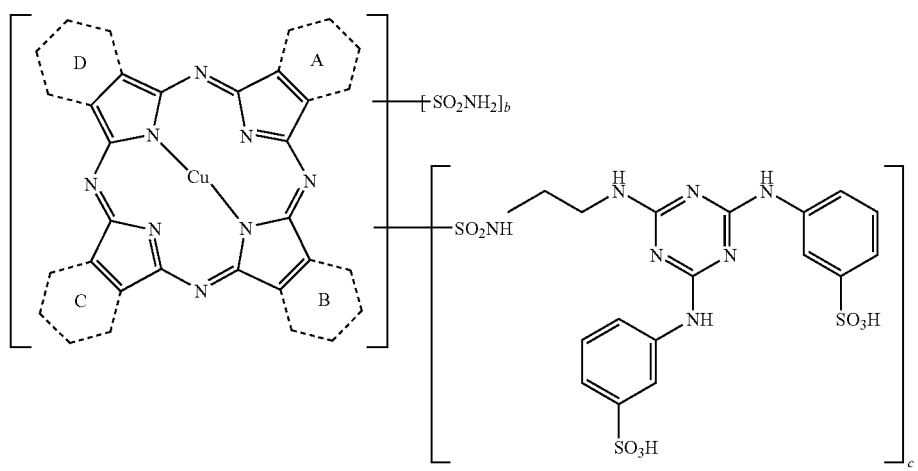

(19)

Comparative Example 4

In the same manner as that of Example 1 except that a coloring matter described in Example 5 of Patent Literature 15 represented by the following formula (20) was used as a coloring matter instead of the porphyrazine coloring matter of the present invention obtained in Example 1, an ink of Comparative Example 4 was prepared.

In this regard, in the following formula (20), 1.5 of the four 6-membered aromatic rings A to D are pyridine rings which are fused at the 2- and 3-positions, and the rest 2.5 are benzene rings.

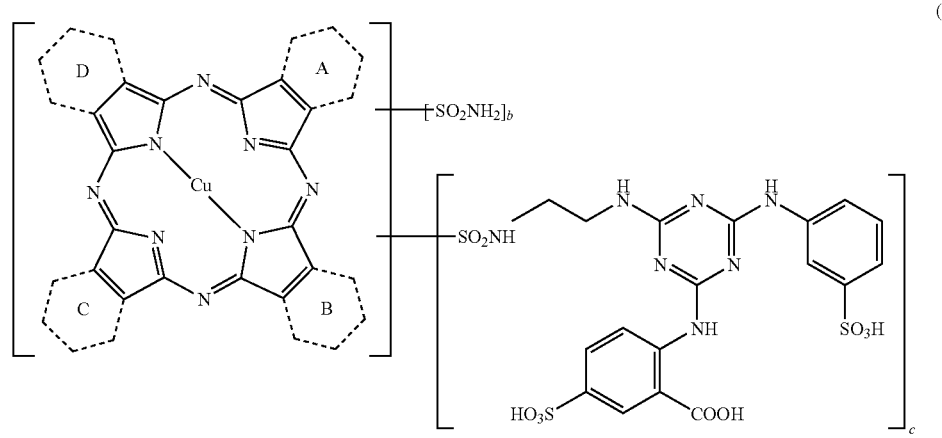

(20)

(B) Inkjet Printing

Using an inkjet printer (manufactured by Canon Inc.; trade name: PIXUS® ip4100), inkjet recording was performed on the 3 kinds of plain paper shown in Table 3 with the inks prepared in Examples 6 to 10 and Comparative Examples 1 to 4. For inkjet recording, a checked pattern (pattern where 1.5 mm-squares having a density of 100% and 1.5 mm-squares having a density of 0% were alternately placed) was made and a printed matter of a cyan-white checked pattern with a high contrast was obtained. In addition, an image pattern was made so that several gradations in reflection density were obtained and a printed matter with a density gradation of cyan was obtained.

TABLE 3

Plain paper 1:

manufactured by Canon Inc.
LBP PAPER LS-500
Plain paper 2:

manufactured by Hewlett Packard
Multipurpose Paper
Plain paper 3:

manufactured by Hewlett Packard
All-in-One Printing Paper

Test methods for recorded images and evaluation methods for test results will be described below.

For judgment by visual observation in water fastness test 1, the above-inkjet printed matter of the checked pattern was used.

For measurement of coloring matter residual rate in water fastness test 2, the above-inkjet printed matter with a gradation for inkjet printing was used, and measurement for reflection density was carried out on the part of the printed matter where the reflection density, D value, was nearest to 1 before the test. In this regard, the reflection density was measured by using a colorimetric system (SpectroEye® manufactured by GretagMacbeth).

(C) Water Fastness Test 1

Each printed matter of the checked pattern dried for 24 hours after printing was immersed in ion-exchanged water for 1 hour. After the printed matter was taken out of the water, it was dried, visually observed for the degree of discoloring of the colored part and the degree of coloring of the white part of the pattern, and evaluated into 3 levels according to the following criteria. The results are shown in Table 4.

Evaluation Criteria:

| | |
|---|---|
| Discoloring is slightly observed. | ○ |
| Discoloring is observed but color remains | Δ |
| Color is all lost. | X |

(D) Water Fastness Test 2

Each printed matter with a gradation dried for 24 hours after printing was immersed in ion-exchanged water for 1 hour. After the printed matter was taken out of the water, it was dried and its reflection density was measured using the above colorimetric system. After the measurement, the coloring matter residual rate was calculated using the following formula and evaluated into 3 levels according to the following criteria. The results are shown in Table 5.

Coloring matter residual rate=(reflection density after test/reflection density before test)×100(%)

Evaluation Criteria:

| | |
|---|---|
| Coloring matter residual rate is 80% or more | ○ |
| Coloring matter residual rate is 50% or more and under 80% | Δ |
| Coloring matter residual rate is under 50% | X |

TABLE 4

Result of Water Fastness Test 1

| | (Plain paper 1) | (Plain paper 2) | (Plain paper 3) |
|---|---|---|---|
| Example 6 | Δ | ◯ | ◯ |
| Example 7 | Δ | ◯ | ◯ |
| Example 8 | Δ | ◯ | ◯ |
| Example 9 | Δ | ◯ | ◯ |
| Example 10 | Δ | ◯ | ◯ |
| Comparative Example 1 | X | X | X |
| Comparative Example 2 | X | X | X |
| Comparative Example 3 | X | X | X |
| Comparative Example 4 | X | X | X |

TABLE 5

Result of water fastness test 2

| | (Plain paper 1) | (Plain paper 2) | (Plain paper 3) |
|---|---|---|---|
| Example 6 | Δ | ◯ | ◯ |
| Example 7 | Δ | ◯ | ◯ |
| Example 8 | Δ | ◯ | ◯ |
| Example 9 | Δ | ◯ | ◯ |
| Example 10 | Δ | ◯ | ◯ |
| Comparative Example 1 | X | X | X |
| Comparative Example 2 | X | X | X |
| Comparative Example 3 | X | X | X |
| Comparative Example 4 | X | X | X |

As is clear from the results of Tables 4 and 5, each Comparative Example has very poor results in all the water fastness tests, showing ink bleeding (water fastness test 1) and a coloring matter residual rate of under 50% (water fastness test 2).

In contrast, it is found that each ink of Examples can get good results in all the water fastness tests 1 and 2, showing that it has extremely high water fastness on plain paper compared with each Comparative Example.

INDUSTRIAL APPLICABILITY

Judging from the above results, the porphyrazine coloring matter of the present invention has high water-solubility and thus is suitable for preparation of ink, particularly for preparation of ink for inkjet recording, and the ink composition of the present invention containing said coloring matter is suitable for ink for inkjet recording because recorded matters (printed matters or colored products) therewith are excellent in various fastnesses particularly when recording (printing or coloring) is performed on a record-receiving material by inkjet and extremely excellent in water fastness particularly when recording (printing or coloring) is performed on plain paper. Due to these characteristics, the porphyrazine coloring matter of the present invention is very useful as a coloring matter for various inks for recording, particularly as a cyan coloring matter for inkjet inks, and the ink composition of the present invention is useful as an ink for inkjet recording.

The invention claimed is:

1. A porphyrazine coloring matter represented by the following formula (1) or a salt thereof:

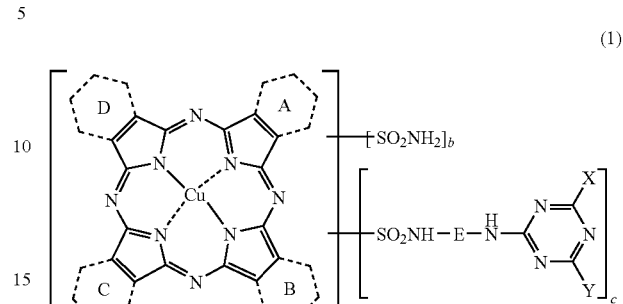

(1)

wherein, the rings A, B, C and D shown by broken lines each independently represent a 6-membered ring having aromaticity, at least 1.0 of said four rings A to D is a benzene ring, and at least 0.5 of the rest is a nitrogen-containing heteroaromatic ring, when shown as an average value;

E represents an alkylene group;

X and Y are each independently an anilino group having 1 to 3 carboxy groups; and b is 0 to 3.4, c is 0.1 to 3.5, and the sum of b and c is 1.0 to 3.5, when shown as an average value.

2. The porphyrazine coloring matter or a salt thereof according to claim 1, wherein the nitrogen-containing heteroaromatic ring is a pyridine ring or a pyrazine ring.

3. The porphyrazine coloring matter or a salt thereof according to claim 1, which is obtained by reaction of a compound represented by the following formula (3) with an organic amine represented by the following formula (4) in the presence of ammonia:

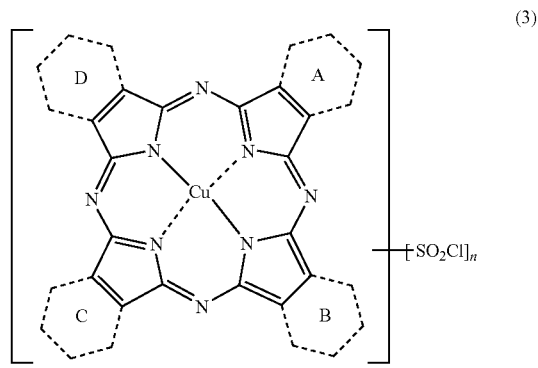

(3)

wherein, the rings A, B, C and D shown by broken lines have the same meanings as those described in claim 1, and n is 1.0 to 3.5 when shown as an average value

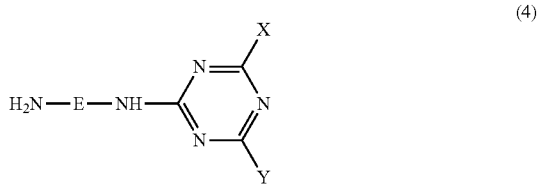

(4)

wherein, E, X and Y have the same meanings as those described in claim 1.

4. The porphyrazine coloring matter or a salt thereof according to claim 1, wherein 0.5 to 3.0 of the four rings A, B, C and D shown by broken lines is a pyridine ring or a pyrazine ring and 1.0 to 3.5 of the rest is a benzene ring, when shown as an average value;

E is a C2-C4 alkylene group;

X and Y are each independently an anilino group having 1 to 3 carboxy groups; and b is 0 to 3.4, c is 0.1 to 3.5 and the sum of b and c is 1.0 to 3.5, when shown as an average value.

5. The porphyrazine coloring matter or a salt thereof according to claim 4, wherein E is an ethylene group or a propylene group.

6. The porphyrazine coloring matter or a salt thereof according to claim 1, wherein 0.5 to 3.0 of the four rings A, B, C and D shown by broken lines is a pyridine ring fused at the 2- and 3-positions or at the 3- and 4-positions, 1.0 to 3.5 of the rest is a benzene ring, when shown as an average value;

E is C2-C4 alkylene;

X and Y are each independently an anilino group having 1 to 3 carboxy groups;

b is 0 to 3.4, c is 0.1 to 3.5 and the sum of b and c is 1.0 to 3.5, when shown as an average value.

7. The porphyrazine coloring matter or a salt thereof according to claim 1 represented by the following formula (2):

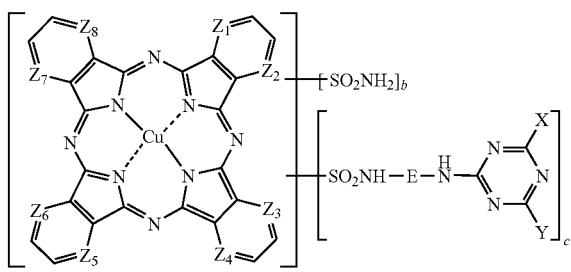

(2)

wherein, $Z_1$ to $Z_8$ each independently represent a nitrogen atom or a carbon atom, at least 1.0 of the 4 combinations of $Z_1$ and $Z_2$, $Z_3$ and $Z_4$, $Z_5$ and $Z_6$, and, $Z_7$ and $Z_8$ is a combination of carbon atoms, at least 0.5 of the rest is a combination of a nitrogen atom and a carbon atom or a combination of nitrogen atoms, when shown as an average value;

E, X, Y, b and c have the same meanings as those of claim 1.

8. The porphyrazine coloring matter or a salt thereof according to claim 7, which is obtained by reaction of a compound represented by the following formula (5) with an organic amine represented by the following formula (4) in the presence of ammonia:

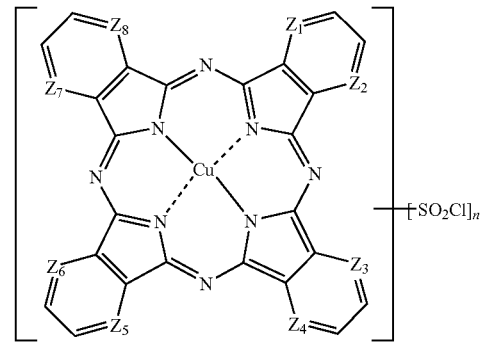

(5)

wherein, $Z_1$ to $Z_8$ have the same meanings as those described in claim 7, and n is 1.0 to 3.5 when shown as an average value

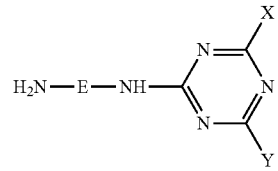

(4)

wherein, E represents an alkylene group; X and Y are each independently an anilino group having 1 to 3 carboxy groups.

9. An ink composition comprising, as a coloring matter component, the porphyrazine coloring matter according to any one of claims 1, 3 and 6.

10. The ink composition according to claim 9, which further contains a water-soluble organic solvent.

11. The ink composition according to claim 10, which is for inkjet recording.

12. A method for inkjet recording comprising discharging an ink droplet of the ink according to claim 1 in response to a recording signal for recording on a record-receiving material.

13. The method for inkjet recording according to claim 12, wherein the record-receiving material is a communication sheet.

14. The method for inkjet recording according to claim 13, wherein the communication sheet is a surface treated sheet and has an ink image-receiving layer containing a white inorganic pigment particle on the support thereof.

15. A container containing the ink composition according to claim 9.

16. An inkjet printer comprising the container according to claim 15.

17. A colored product colored with the porphyrazine coloring matter according to claim 1.

18. A colored product colored with the ink composition according to claim 9.

* * * * *